(12) United States Patent
Setliff et al.

(10) Patent No.: US 12,416,037 B2
(45) Date of Patent: Sep. 16, 2025

(54) METHODS FOR IDENTIFICATION OF LIGAND-BLOCKING ANTIBODIES AND FOR DETERMINING ANTIBODY POTENCY

(71) Applicant: Vanderbilt University, Nashville, TN (US)

(72) Inventors: Marion Francis Setliff, Nashville, TN (US); Ivelin Stefanov Georgiev, Brentwood, TN (US); Andrea Shiakolas, Nashville, TN (US); Kelsey Pilewski, Nashville, TN (US); Rohit Venkat, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 655 days.

(21) Appl. No.: 17/795,104

(22) PCT Filed: Jan. 22, 2021

(86) PCT No.: PCT/US2021/014514
§ 371 (c)(1),
(2) Date: Jul. 25, 2022

(87) PCT Pub. No.: WO2021/150821
PCT Pub. Date: Jul. 29, 2021

(65) Prior Publication Data
US 2022/0372551 A1    Nov. 24, 2022
US 2023/0242966 A9    Aug. 3, 2023

Related U.S. Application Data

(60) Provisional application No. 62/965,257, filed on Jan. 24, 2020.

(51) Int. Cl.
C12Q 1/68       (2018.01)
C07K 16/10      (2006.01)
(Continued)

(52) U.S. Cl.
CPC ........ *C12Q 1/6806* (2013.01); *C07K 16/1063* (2013.01); *C12Q 1/703* (2013.01); *C07K 2317/76* (2013.01)

(58) Field of Classification Search
None
See application file for complete search history.

(56) References Cited

U.S. PATENT DOCUMENTS 4,342,566 A    8/1982    Theofilopoulos et al.
5,079,155 A    1/1992    Cox et al.
(Continued)

FOREIGN PATENT DOCUMENTS

AU    2017326338 A1    1/2019
WO    94/29348          12/1994
(Continued)

OTHER PUBLICATIONS

Partial Supplementary European Search Report issued for Application No. 21744089, dated Jan. 25, 2024.
(Continued)

*Primary Examiner* — Aaron A Priest
(74) *Attorney, Agent, or Firm* — Meunier Carlin & Curfman LLC

(57) ABSTRACT

The present disclosure relates to high-throughput systems and methods for the detection of ligand-blocking antibodies and for determining antibody potency.

17 Claims, 19 Drawing Sheets

Specification includes a Sequence Listing.

(51) Int. Cl.
  *C12Q 1/6806* (2018.01)
  *C12Q 1/70* (2006.01)

(56) References Cited

U.S. PATENT DOCUMENTS

| | | | |
|---|---|---|---|
| 5,084,169 | A | 1/1992 | Noble et al. |
| 5,473,231 | A | 12/1995 | McLaughlin et al. |
| 5,804,440 | A | 9/1998 | Burton et al. |
| 6,096,441 | A | 8/2000 | Hauser et al. |
| 8,110,351 | B2 | 2/2012 | Bosnes |
| 2016/0265046 | A1 | 9/2016 | Zhang et al. |
| 2018/0105808 | A1 | 4/2018 | Mikkelsen et al. |
| 2018/0127743 | A1 | 5/2018 | Vigneault et al. |
| 2018/0216160 | A1 | 8/2018 | Abate et al. |
| 2018/0251825 | A1 | 9/2018 | Stoeckius et al. |
| 2019/0025299 | A1 | 1/2019 | Vigneault et al. |

FOREIGN PATENT DOCUMENTS

| | | | | |
|---|---|---|---|---|
| WO | WO-2018057051 | A1 * | 3/2018 | ......... C12N 15/1065 |
| WO | 2019084055 | A1 | 5/2019 | |
| WO | 2020033164 | | 2/2020 | |
| WO | 2020033164 | A1 | 2/2020 | |
| WO | 2020206232 | A1 | 10/2020 | |

OTHER PUBLICATIONS

International Search Report and Written Opinion received in PCT/US2021/014514, dated Jun. 3, 2021, 15 pages.
Ian Setliff et al. High-Throughput Mapping of B Cell Receptor Sequences to Antigen Specificity, Cell, Dec. 12, 2019, vol. 179, No. 7, pp. 1636-1646. Especially p. 1637 col. 1 para 2, p. 1637 col. 2 para 1, p. 1637 col. 1 para 3, p. 1643 col. 2 para 2, p. 1642 col. 2 para 2, p. e5 para 5, p. e5 para 3, p. e5 para 7, p. e6 para 1, p. e6 para 2, p. e6 para 3, p. e6 para 4, Figure 1, Figure 2B, Figure 3C, Figure 4, Figure SA, Figure S1B, Figure SSA, Abstract.
Extended Search Report issued for European Application No. 21744089, dated Apr. 15, 2024.
Extended European Search report issued for Application No. 20860107, dated Sep. 18, 2023.
International Preliminary Report on Patentability issue for Application No. PCT/US2020/049330, dated Mar. 8, 2022.
International Search Report and Written Opinion dated Dec. 12, 2020, from International Application No. PCT/US2020/049330, 13 pages.
International Preliminary Report on Patentability for International Application No. PCT/US2021/014514 dated Aug. 4, 2022, 11 pages.
Ackerman, Margaret E., et al. "A robust, high-throughput assay to determine the phagocytic activity of clinical antibody samples." Journal of immunological methods 366.1-2 (2011): 8-19.
Adam S. Adler, et al., (2017) "Rare, high-affinity mouse anti-PD-1 antibodies that function in checkpoint blockade, discovered using microfluidics and molecular genomics", mAbs, 9:8, 1270-1281, DOI: 10.1080/19420862.2017.1371386.
Adler, Adam S., et al. "Rare, high-affinity anti-pathogen antibodies from human repertoires, discovered using microfluidics and molecular genomics." MAbs. vol. 9. No. 8. Taylor & Francis, 2017. 9:8, 1282-1296.
Alamyar, Eltaf, et al. "IMGT/HighV-Quest: the IMGT® web portal for immunoglobulin (IG) or antibody and T cell receptor (TR) analysis from NGS high throughput and deep sequencing." Immunome research 8.1 (2012): 26.
Bonsignori, Mattia, et al. "Inference of the HIV-1 VRC01 antibody lineage unmutated common ancestor reveals alternative pathways to overcome a key glycan barrier." Immunity 49.6 (2018): 1162-1174.
Brekke, Ole Henrik, and Inger Sandlie. "Therapeutic antibodies for human diseases at the dawn of the twenty-first century." Nature reviews Drug discovery 2.1 (2003): 52-62.

Briney, Bryan, et al. "Commonality despite exceptional diversity in the baseline human antibody repertoire." Nature 566.7744 (2019): 393-397.
Buchacher, A., et al. "Generation of human monoclonal antibodies against HIV-1 proteins; electrofusion and Epstein-Barr virus transformation for peripheral blood lymphocyte immortalization." AIDS research and human retroviruses 10.4 (1994): 359-369.
Busse, Christian E., et al. "Single-cell based high-throughput sequencing of full-length immunoglobulin heavy and light chain genes." European journal of immunology 44.2 (2014): 597-603.
Cale, Evan M., et al. "Virus-like particles identify an HIV V1V2 apex-binding neutralizing antibody that lacks a protruding loop." Immunity 46.5 (2017): 777-791.
Chen, Shifu, et al. "fastp: an ultra-fast all-in-one FASTQ preprocessor." Bioinformatics 34.17 (2018): i884-i890.
Crooke, Stanley T., et al. "Pharmacokinetic properties of several novel oligonucleotide analogs in mice." Journal of Pharmacology and Experimental Therapeutics 277.2 (1996): 923-937.
DeCamp, Allan, et al. "Global panel of HIV-1 Env reference strains for standardized assessments of vaccine-elicited neutralizing antibodies." Journal of virology 88.5 (2014): 2489-2507.
DeFalco, Jeff, et al. "Non-progressing cancer patients have persistent B cell responses expressing shared antibody paratopes that target public tumor antigens." Clinical Immunology 187 (2018): 37-45.
DeKosky, Brandon J., et al. "High-throughput sequencing of the paired human immunoglobulin heavy and light chain repertoire." Nature biotechnology 31.2 (2013): 166-169.
Do Kwon, Young, et al. "Crystal structure, conformational fixation and entry-related interactions of mature ligand-free HIV-1 Env." Nature structural & molecular biology 22.7 (2015): 522-531.
Dosenovic, Pia, et al. "Anti-idiotypic antibodies elicit anti-HIV-1-specific B cell responses." Journal of Experimental Medicine 216. 10 (2019): 2316-2330.
Georgiev, Ivelin S., et al. "Single-chain soluble BG505. SOSIP gp140 trimers as structural and antigenic mimics of mature closed HIV-1 Env." Journal of virology 89.10 (2015): 5318-5329.
Georgiou, George, et al. "The promise and challenge of high-throughput sequencing of the antibody repertoire." Nature biotechnology 32.2 (2014): 158-168.
Goldstein et al., "Massively parallel single-cell B-cell receptor sequencing enables rapid discovery of diverse antigen-reactive antibodies" Communications Biology, https://doi.org/10.1038/s42003-019-0551-y.
Guindon, Stéphane, et al. "Estimating maximum likelihood phylogenies with PhyML." Bioinformatics for DNA sequence analysis. Humana Press, 2009. 113-137.
Gupta, Namita T., et al. "Change-O: a toolkit for analyzing large-scale B cell immunoglobulin repertoire sequencing data." Bioinformatics 31.20 (2015): 3356-3358.
Harris, Audray, et al. "Trimeric HIV-1 glycoprotein gp140 immunogens and native HIV-1 envelope glycoproteins display the same closed and open quaternary molecular architectures." Proceedings of the National Academy of Sciences 108.28 (2011): 11440-11445.
Huang, Jinghe, et al. "Broad and potent HIV-1 neutralization by a human antibody that binds the gp41-gp120 interface." Nature 515.7525 (2014): 138-142.
Jardine, Joseph G., et al. "HIV-1 broadly neutralizing antibody precursor B cells revealed by germline-targeting immunogen." Science 351.6280 (2016): 1458-1463.
Jardine, Joseph, et al. "Rational HIV immunogen design to target specific germline B cell receptors." Science 340.6133 (2013): 711-716.
Joyce, M. Gordon, et al. "Soluble prefusion closed DS-SOSIP. 664-Env trimers of diverse HIV-1 strains." Cell reports 21.10 (2017): 2992-3002.
Julien, Jean-Philippe, et al. "Design and structure of two HIV-1 clade C SOSIP. 664 trimers that increase the arsenal of native-like Env immunogens." Proceedings of the National Academy of Sciences 112.38 (2015): 11947-11952.
Kabanov, Alexander V., et al. "A new class of antivirals: antisense oligonucleotides combined with a hydrophobic substituent effec-

(56) References Cited

OTHER PUBLICATIONS tively inhibit influenza virus reproduction and synthesis of virus-specific proteins in MDCK cells." FEBS letters 259.2 (1990): 327-330.
Köhler, Georges, and Cesar Milstein. "Continuous cultures of fused cells secreting antibody of predefined specificity." nature 256.5517 (1975): 495-497.
Kotecha, Nikesh, Peter O. Krutzik, and Jonathan M. Irish. "Web-based analysis and publication of flow cytometry experiments." Current protocols in cytometry 53.1 (2010): 10-17.
Letsinger, Robert L., et al. "Cholesteryl-conjugated oligonucleotides: synthesis, properties, and activity as inhibitors of replication of human immunodeficiency virus in cell culture." Proceedings of the National Academy of Sciences 86.17 (1989): 6553-6556.
Letunic, Ivica, and Peer Bork. "Interactive Tree of Life (iTOL) v4: recent updates and new developments." Nucleic acids research 47.W1 (2019): W256-W259.
Lingwood, Daniel, et al. "Structural and genetic basis for development of broadly neutralizing influenza antibodies." Nature 489.7417 (2012): 566-570.
Manoharan, M., et al. "Chemical modifications to improve uptake and bioavailability of antisense oligonucleotides." Annals of the New York Academy of Sciences 660.1 (1992): 306-309.
Manoharan, Muthiah, et al. "Cholic acid-oligonucleotide conjugates for antisense applications." Bioorganic & Medicinal Chemistry Letters 4.8 (1994): 1053-1060.
Manoharan, Muthiah, et al. "Introduction of a lipophilic thioether tether in the minor groove of nucleic acids for antisense applications." Bioorganic & Medicinal Chemistry Letters 3.12 (1993): 2765-2770.
Manoharan, Muthiah, Kathleen L. Tivel, and P. Dan Cook. "Lipidic nucleic acids." Tetrahedron Letters 36.21 (1995): 3651-3654.
Mimitou, Eleni P., et al. "Multiplexed detection of proteins, transcriptomes, clonotypes and CRISPR perturbations in single cells." Nature methods 16.5 (2019): 409-412.
Mishra, Rakesh Kumar, et al. "Improved leishmanicidal effect of phosphorotioate antisense oligonucleotides by LDL-mediated delivery." Biochimica et Biophysica Acta (BBA)—Gene Structure and Expression 1264.2 (1995): 229-237.
Oberhauser, Berndt, and Ernst Wagner. "Effective incorporation of 2'-O-methyl-oligoribonucleotides into liposomes and enhanced cell association through modification with thiocholesterol." Nucleic Acids Research 20.3 (1992): 533-538.
Pedregosa, Fabian, et al. "Scikit-learn: Machine learning in Python." the Journal of machine Learning research 12 (2011): 2825-2830.
Peterson, Vanessa M., et al. "Multiplexed quantification of proteins and transcripts in single cells." Nature biotechnology 35.10 (2017): 936-939.
Pollara, Justin, et al. "High-throughput quantitative analysis of HIV-1 and SIV-specific ADCC-mediating antibody responses." Cytometry Part A 79.8 (2011): 603-612.
Pugach, Pavel, et al. "A native-like SOSIP. 664 trimer based on an HIV-1 subtype B env gene." Journal of virology 89.6 (2015): 3380-3395.
Rajewsky, Klaus. "Clonal selection and learning in the antibody system." Nature 381.6585 (1996): 751-758.
Richardson, Simone I., et al. "HIV-specific Fc effector function early in infection predicts the development of broadly neutralizing antibodies." PLoS pathogens 14.4 (2018): e1006987.
Richardson, Simone I., et al. "Measuring the ability of HIV-specific antibodies to mediate trogocytosis." Journal of immunological methods 463 (2018): 71-83.
Ringe, Rajesh P., et al. "Improving the expression and purification of soluble, recombinant native-like HIV-1 envelope glycoprotein trimers by targeted sequence changes." Journal of virology 91.12 (2017): e00264-17.
Sanders, Rogier W., et al. "A next-generation cleaved, soluble HIV-1 Env trimer, BG505 SOSIP. 664 gp140, expresses multiple epitopes for broadly neutralizing but not non-neutralizing antibodies." PLoS pathogens 9.9 (2013): e1003618.
Sarzotti-Kelsoe, Marcella, et al. "Optimization and validation of the TZM-bl assay for standardized assessments of neutralizing antibodies against HIV-1." Journal of immunological methods 409 (2014): 131-146.
Scheid, Johannes F., et al. "Broad diversity of neutralizing antibodies isolated from memory B cells in HIV-infected individuals." Nature 458.7238 (2009): 636-640.
Setliff, Ian, et al. "Multi-donor longitudinal antibody repertoire sequencing reveals the existence of public antibody clonotypes in HIV-1 infection." Cell host & microbe 23.6 (2018): 845-854.
Shea, Regan G., James C. Marsters, and Norbert Bischofberger. "Synthesis, hybridization properties and antiviral activity of lipid-oligodeoxynucleotide conjugates." Nucleic acids research 18.13 (1990): 3777-3783.
Soto, Cinque, et al. "High frequency of shared clonotypes in human B cell receptor repertoires." Nature 566.7744 (2019): 398-402.
Stamatatos, Leonidas, Marie Pancera, and Andrew T. McGuire. "Germline-targeting immunogens." Immunological reviews 275.1 (2017): 203-216.
Stiegler, Gabriela, et al. "A potent cross-clade neutralizing human monoclonal antibody against a novel epitope on gp41 of human immunodeficiency virus type 1." AIDS research and human retroviruses 17.18 (2001): 1757-1765.
Stoeckius, Marlon, et al. "Cell Hashing with barcoded antibodies enables multiplexing and doublet detection for single cell genomics." Genome biology 19.1 (2018): 224, 1-12.
Stoeckius, Marlon, et al. "Simultaneous epitope and transcriptome measurement in single cells." Nature methods 14.9 (2017): 865-868.
Svinarchuk, F. P., et al. "Inhibition of HIV proliferation in MT-4 cells by antisense oligonucleotide conjugated to lipophilic groups." Biochimie 75.1-2 (1993): 49-54.
Tan, Yann-Chong, et al. "Barcode-enabled sequencing of plasmablast antibody repertoires in rheumatoid arthritis." Arthritis & rheumatology 66.10 (2014): 2706-2715.
Walker, Laura M., et al. "Broad and potent neutralizing antibodies from an African donor reveal a new HIV-1 vaccine target." Science 326.5950 (2009): 285-289.
Walker, Laura M., et al. "Broad neutralization coverage of HIV by multiple highly potent antibodies." Nature 477.7365 (2011): 466-470.
Wang, Bo, et al. "Functional interrogation and mining of natively paired human VH: VL antibody repertoires." Nature biotechnology 36.2 (2018): 152-155.
Weaver, Grant C., et al. "In vitro reconstitution of B cell receptor-antigen interactions to evaluate potential vaccine candidates." Nature protocols 11.2 (2016): 193-213.
Whittle, James RR, et al. "Flow cytometry reveals that H5N1 vaccination elicits cross-reactive stem-directed antibodies from multiple Ig heavy-chain lineages." Journal of virology 88.8 (2014): 4047-4057.
Wilson, Patrick C., and Sarah F. Andrews. "Tools to therapeutically harness the human antibody response." Nature Reviews Immunology 12.10 (2012): 709-719.
Wu, Xueling, et al. "Maturation and diversity of the VRC01-antibody lineage over 15 years of chronic HIV-1 infection." Cell 161.3 (2015): 470-485.
Wu, Xueling, et al. "Rational design of envelope identifies broadly neutralizing human monoclonal antibodies to HIV-1." Science 329.5993 (2010): 856-861.
Wu, Xueling, et al. "Selection pressure on HIV-1 envelope by broadly neutralizing antibodies to the conserved CD4-binding site." Journal of virology 86.10 (2012): 5844-585.
Zoller, Mark J. "New recombinant DNA methodology for protein engineering." Current opinion in biotechnology 3.4 (1992): 348-354.

\* cited by examiner

| Antibody | Clonally Expanded? | VH Gene | VH Identity | CDRH3 Sequence | CDRH3 Length | VL Gene | VL Identity | CDRL3 Sequence | CDRL3 Length |
|---|---|---|---|---|---|---|---|---|---|
| 53181-1 | yes - 7* | IGHV1-18 | 0.9653 | CARDPASYYDFWSGYVDYYYYGMDVW | 24 | IGKV3-20 | 0.9858 | CQQYGNSRLTF | 9 |
| 53181-2 | yes - 7* | IGHV1-18 | 0.9896 | CARDPASYYDLWSGYVDYYYYGMDVW | 24 | IGKV3-20 | 0.9929 | CHHYGSSRLTF | 9 |
| 53181-3 | yes - 4 | IGHV1-69 | 0.9062 | CARSGGYRLWFGELW | 13 | IGKV3-20 | 0.9362 | CQQYGGSPATF | 9 |
| 53181-4 | yes - 9 | IGHV3-33 | 0.9792 | CAREGAVGATSGLDYW | 14 | IGLV3-10 | 0.9928 | CYSRDSSGNPLF | 10 |
| 53181-5 | yes - 6 | IGHV4-59 | 0.9509 | CARGFDYW | 6 | IGKV3-20 | 0.9752 | CQQYGSSPWTF | 9 |
| 53181-6 | yes - 3 | IGHV4-59 | 0.9439 | CARGAGEQRLVGGLFGVSHFYYYMDVW | 25 | IGKV1-5 | 0.9928 | CQQYNSYPWTF | 9 |
| 53181-7 | no | IGHV3-23 | 0.9375 | CAKSATIVLMVSAIYW | 14 | IGLV2-14 | 0.9653 | CSSYTSTSTLVF | 10 |
| 53181-8 | no | IGHV3-72 | 0.9864 | CARVRGGEWVGDLGWYYYYGMDVW | 22 | IGKV2-28 | 0.9932 | CMQALQTPRTF | 9 |
| 53181-9 | yes - 14 | IGHV3-30 | 0.9062 | CVKGATKIDYW | 9 | IGLV2-14 | 0.9062 | CFSYTSGGTRVF | 10 |
| 53171-1 | no | IGHV1-58 | 0.9479 | CAADPFADYW | 8 | IGLV1-44 | 0.9754 | CATWDDSLNAWVF | 11 |
| 53171-2 | no | IGHV1-69 | 0.9479 | CARGLWFGDSETVWFDPW | 16 | IGKV1-39 | 0.9677 | CQQSYSTPPTF | 9 |
| 53171-3 | no | IGHV3-64D | 0.9306 | CVKGKIQLWLGADYW | 13 | IGKV1-39 | 0.9677 | CQQSYNTPWTF | 9 |
| 53171-4 | yes - 2 | IGHV4-34 | 0.9263 | CARKPLLHSSVNPGAFDIW | 17 | IGKV3-20 | 0.9645 | CQQYATSPRTF | 9 |
| 53171-5 | yes - 5 | IGHV1-69 | 0.9653 | CAREKGYSSSSATYYLDFW | 18 | IGLV1-40 | 0.9757 | CQSYDSSLTALVF | 11 |
| 53171-6 | no | IGHV4-39 | 0.9691 | CARRVPGDYYCLDVW | 13 | IGKV1-39 | 0.9606 | CQQSFSARVPTF | 10 |
| 53171-7 | yes - 3 | IGHV3-7 | 0.9722 | CARGGLWGTFDYW | 11 | IGKV3-20 | 0.9752 | CQQFAYSLYTF | 9 |
| 53171-8 | yes - 4 | IGHV3-30-3 | 0.9583 | CARAYGGNYYYGMDVW | 14 | IGLV3-1 | 0.9606 | CQAWDSSTASFVF | 11 |
| 53171-9 | yes - 3 | IGHV1-69 | 0.9479 | CASLGGDSYISGTHYDRSGYDPW | 21 | IGKV3-11 | 0.9821 | CQRRSNWPPFTF | 10 |
| 53171-10 | yes - 4 | IGHV5-10-1 | 0.9271 | CARVNRVGDGPDFW | 12 | IGKV2-28 | 0.966 | CMQALQTPWTF | 9 |
| 53182-1 | yes - 3 | IGHV3-53 | 0.9544 | CTRGGWPSGDTFDIW | 13 | IGKV1-9 | 0.9928 | CQQLNSYPEITF | 10 |
| 53182-2 | no | IGHV3-48 | 0.9757 | CAREGGWYSVGWVDPW | 14 | IGKV3-20 | 0.9752 | CQQYGSSRTF | 8 |
| 53182-3 | yes - 6 | IGHV3-66 | 0.9895 | CARDRRIIGYYFGMDVW | 15 | IGLV2-23 | 0.9688 | CCPYADTWVF | 9 |
| 53182-4 | yes - 3 | IGHV2-5 | 0.8522 | CARLLIEHDAFDIW | 12 | IGKV2-28 | 0.9184 | CMQALHFPYTF | 10 |
| 53182-5 | no | IGHV1-69 | 0.9474 | CAREEGSGWWKHDYW | 13 | IGLV2-23 | 0.9617 | CQQLSGPYTF | 9 |
| 53182-6 | yes - 6 | IGHV3-66 | 0.9757 | CVRDRRIVGYYFGLDVW | 15 | IGKV3-20 | 0.9618 | CCSYATTWVF | 8 |
| 53182-7 | no | IGHV3-23 | 0.9897 | CAKDAFYYGSGSHFYYYYMDVW | 21 | IGKV2-23 | 0.9894 | CQQYGSSPTF | 9 |
| 53182-8 | yes - 6 | IGHV4-39 | 0.9754 | CARDRRGGGWTASFDFW | 15 | IGKV4-1 | 0.9933 | CQQHYSTPGYTF | 10 |
| 53182-9 | yes - 3 | IGHV3-53 | 0.9897 | CARGGWPSGDTFDIW | 13 | IGKV1-9 | 0.9928 | CQQLNSYPEITF | 10 |
| 53182-10 | yes - 2 | IGHV2-5 | 0.9794 | CAHHTVPTIYDYW | 11 | IGLV2-8 | 0.9826 | CSSYAGSNPLVF | 10 |
| 53182-11 | yes - 12 | IGHV3-9 | 0.9271 | CAKDIGRYDHYNIFGRVGGAFDIW | 22 | IGKV1-33 | 0.9534 | CQHYDNLPRF | 8 |

FIGS. 17A-17C

SEQUENCE LISTING

<160> NUMBER OF SEQ ID NOS: 59

<210> SEQ ID NO 1
<211> LENGTH: 26
<212> TYPE: PRT

```
<213> ORGANISM: Artificial Sequence
<220> FEATURE:
<223> OTHER INFORMATION: Synthetic construct

<400> SEQUENCE: 1

Cys Ala Arg Asp Pro Ala Ser Tyr Tyr Asp Phe Trp Ser Gly Tyr Val
1               5                   10                  15

Asp Tyr Tyr Tyr Tyr Gly Met Asp Val Trp
            20                  25

<210> SEQ ID NO 2
<211> LENGTH: 26
<212> TYPE: PRT
<213> ORGANISM: Artificial Sequence
<220> FEATURE:
<223> OTHER INFORMATION: Synthetic construct

<400> SEQUENCE: 2

Cys Ala Arg Asp Pro Ala Ser Tyr Tyr Asp Leu Trp Ser Gly Tyr Val
1               5                   10                  15

Asp Tyr Tyr Tyr Tyr Gly Met Asp Val Trp
            20                  25

<210> SEQ ID NO 3
<211> LENGTH: 15
<212> TYPE: PRT
<213> ORGANISM: Artificial Sequence
<220> FEATURE:
<223> OTHER INFORMATION: Synthetic construct

<400> SEQUENCE: 3

Cys Ala Arg Ser Gly Gly Tyr Arg Leu Trp Phe Gly Glu Leu Trp
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Synthetic construct

<400> SEQUENCE: 4

Cys Ala Arg Glu Gly Ala Val Gly Ala Thr Ser Gly Leu Asp Tyr Trp
1               5                   10                  15

<210> SEQ ID NO 5
<211> LENGTH: 8
<212> TYPE: PRT
<213> ORGANISM: Artificial Sequence
<220> FEATURE:
<223> OTHER INFORMATION: Synthetic construct

<400> SEQUENCE: 5

Cys Ala Arg Gly Phe Asp Tyr Trp
1               5

<210> SEQ ID NO 6
<211> LENGTH: 27
<212> TYPE: PRT
<213> ORGANISM: Artificial Sequence
<220> FEATURE:
<223> OTHER INFORMATION: Synthetic construct

<400> SEQUENCE: 6

Cys Ala Arg Gly Ala Gly Glu Gln Arg Leu Val Gly Gly Leu Phe Gly
1               5                   10                  15
```

Val Ser His Phe Tyr Tyr Tyr Met Asp Val Trp
            20                  25

<210> SEQ ID NO 7
<211> LENGTH: 16
<212> TYPE: PRT
<213> ORGANISM: Artificial Sequence
<220> FEATURE:
<223> OTHER INFORMATION: Synthetic construct

<400> SEQUENCE: 7

Cys Ala Lys Ser Ala Thr Ile Val Leu Met Val Ser Ala Ile Tyr Trp
1               5                   10                  15

<210> SEQ ID NO 8
<211> LENGTH: 24
<212> TYPE: PRT
<213> ORGANISM: Artificial Sequence
<220> FEATURE:
<223> OTHER INFORMATION: Synthetic construct

<400> SEQUENCE: 8

Cys Ala Arg Val Arg Gly Gly Glu Trp Val Gly Asp Leu Gly Trp Tyr
1               5                   10                  15

Tyr Tyr Tyr Gly Met Asp Val Trp
            20

<210> SEQ ID NO 9
<211> LENGTH: 11
<212> TYPE: PRT
<213> ORGANISM: Artificial Sequence
<220> FEATURE:
<223> OTHER INFORMATION: Synthetic construct

<400> SEQUENCE: 9

Cys Val Lys Gly Ala Thr Lys Ile Asp Tyr Trp
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic construct

<400> SEQUENCE: 10

Cys Gln Gln Tyr Gly Asn Ser Arg Leu Thr Phe
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic construct

<400> SEQUENCE: 11

Cys His His Tyr Gly Ser Ser Arg Leu Thr Phe
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic construct

<400> SEQUENCE: 12

Cys Gln Gln Tyr Gly Gly Ser Pro Ala Thr Phe
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic construct

<400> SEQUENCE: 13

Cys Tyr Ser Arg Asp Ser Ser Gly Asn Pro Leu Phe
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic construct

<400> SEQUENCE: 14

Cys Gln Gln Tyr Gly Ser Ser Pro Trp Thr Phe
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Synthetic construct

<400> SEQUENCE: 15

Cys Gln Gln Tyr Asn Ser Tyr Pro Trp Thr Phe
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic construct

<400> SEQUENCE: 16

Cys Ser Ser Tyr Thr Ser Thr Ser Thr Leu Val Phe
1               5                   10

<210> SEQ ID NO 17
<211> LENGTH: 11
<212> TYPE: PRT
<213> ORGANISM: Artificial Sequence
<220> FEATURE:
<223> OTHER INFORMATION: Synthetic construct

<400> SEQUENCE: 17

Cys Met Gln Ala Leu Gln Thr Pro Arg Thr Phe
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic construct

```
<400> SEQUENCE: 18

Cys Phe Ser Tyr Thr Ser Gly Gly Thr Arg Val Phe
1               5                   10

<210> SEQ ID NO 19
<211> LENGTH: 10
<212> TYPE: PRT
<213> ORGANISM: Artificial Sequence
<220> FEATURE:
<223> OTHER INFORMATION: Synthetic construct

<400> SEQUENCE: 19

Cys Ala Ala Asp Pro Phe Ala Asp Tyr Trp
1               5                   10

<210> SEQ ID NO 20
<211> LENGTH: 18
<212> TYPE: PRT
<213> ORGANISM: Artificial Sequence
<220> FEATURE:
<223> OTHER INFORMATION: Synthetic construct

<400> SEQUENCE: 20

Cys Ala Arg Gly Leu Trp Phe Gly Asp Ser Glu Thr Val Trp Phe Asp
1               5                   10                  15

Pro Trp

<210> SEQ ID NO 21
<211> LENGTH: 15
<212> TYPE: PRT
<213> ORGANISM: Artificial Sequence
<220> FEATURE:
<223> OTHER INFORMATION: Synthetic construct

<400> SEQUENCE: 21

Cys Val Lys Gly Lys Ile Gln Leu Trp Leu Gly Ala Asp Tyr Trp
1               5                   10                  15

<210> SEQ ID NO 22
<211> LENGTH: 19
<212> TYPE: PRT
<213> ORGANISM: Artificial Sequence
<220> FEATURE:
<223> OTHER INFORMATION: Synthetic construct

<400> SEQUENCE: 22

Cys Ala Arg Lys Pro Leu Leu His Ser Ser Val Asn Pro Gly Ala Phe
1               5                   10                  15

Asp Ile Trp

<210> SEQ ID NO 23
<211> LENGTH: 20
<212> TYPE: PRT
<213> ORGANISM: Artificial Sequence
<220> FEATURE:
<223> OTHER INFORMATION: Synthetic construct

<400> SEQUENCE: 23

Cys Ala Arg Glu Lys Gly Tyr Ser Ser Ser Ser Ala Thr Tyr Tyr
1               5                   10                  15

Leu Asp Phe Trp
            20

<210> SEQ ID NO 24
```

```
<211> LENGTH: 15
<212> TYPE: PRT
<213> ORGANISM: Artificial Sequence
<220> FEATURE:
<223> OTHER INFORMATION: Synthetic construct

<400> SEQUENCE: 24

Cys Ala Arg Arg Val Pro Gly Asp Tyr Tyr Cys Leu Asp Val Trp
1               5                   10                  15

<210> SEQ ID NO 25
<211> LENGTH: 13
<212> TYPE: PRT
<213> ORGANISM: Artificial Sequence
<220> FEATURE:
<223> OTHER INFORMATION: Synthetic construct

<400> SEQUENCE: 25

Cys Ala Arg Gly Gly Leu Trp Gly Thr Phe Asp Tyr Trp
1               5                   10

<210> SEQ ID NO 26
<211> LENGTH: 16
<212> TYPE: PRT
<213> ORGANISM: Artificial Sequence
<220> FEATURE:
<223> OTHER INFORMATION: Synthetic construct

<400> SEQUENCE: 26

Cys Ala Arg Ala Tyr Gly Gly Asn Tyr Tyr Tyr Gly Met Asp Val Trp
1               5                   10                  15

<210> SEQ ID NO 27
<211> LENGTH: 23
<212> TYPE: PRT
<213> ORGANISM: Artificial Sequence
<220> FEATURE:
<223> OTHER INFORMATION: Synthetic construct

<400> SEQUENCE: 27

Cys Ala Ser Leu Gly Gly Asp Ser Tyr Ile Ser Gly Thr His Tyr Asp
1               5                   10                  15

Arg Ser Gly Tyr Asp Pro Trp
            20

<210> SEQ ID NO 28
<211> LENGTH: 14
<212> TYPE: PRT
<213> ORGANISM: Artificial Sequence
<220> FEATURE:
<223> OTHER INFORMATION: Synthetic construct

<400> SEQUENCE: 28

Cys Ala Arg Val Asn Arg Val Gly Asp Gly Pro Asp Phe Trp
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Synthetic construct

<400> SEQUENCE: 29

Cys Ala Thr Trp Asp Asp Ser Leu Asn Ala Trp Val Phe
1               5                   10
```

```
<210> SEQ ID NO 30
<211> LENGTH: 11
<212> TYPE: PRT
<213> ORGANISM: Artificial Sequence
<220> FEATURE:
<223> OTHER INFORMATION: Synthetic construct

<400> SEQUENCE: 30

Cys Gln Gln Ser Tyr Ser Thr Pro Pro Thr Phe
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic construct

<400> SEQUENCE: 31

Cys Gln Gln Ser Tyr Asn Thr Pro Trp Thr Phe
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic construct

<400> SEQUENCE: 32

Cys Gln Gln Tyr Ala Thr Ser Pro Arg Thr Phe
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Synthetic construct

<400> SEQUENCE: 33

Cys Gln Ser Tyr Asp Ser Ser Leu Thr Ala Leu Val Phe
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic construct

<400> SEQUENCE: 34

Cys Gln Gln Ser Phe Ser Ala Arg Val Pro Thr Phe
1               5                   10

<210> SEQ ID NO 35
<211> LENGTH: 11
<212> TYPE: PRT
<213> ORGANISM: Artificial Sequence
<220> FEATURE:
<223> OTHER INFORMATION: Synthetic construct

<400> SEQUENCE: 35

Cys Gln Gln Phe Ala Tyr Ser Leu Tyr Thr Phe
1               5                   10
```

```
<210> SEQ ID NO 36
<211> LENGTH: 13
<212> TYPE: PRT
<213> ORGANISM: Artificial Sequence
<220> FEATURE:
<223> OTHER INFORMATION: Synthetic construct

<400> SEQUENCE: 36

Cys Gln Ala Trp Asp Ser Ser Thr Ala Ser Phe Val Phe
1               5                   10

<210> SEQ ID NO 37
<211> LENGTH: 12
<212> TYPE: PRT
<213> ORGANISM: Artificial Sequence
<220> FEATURE:
<223> OTHER INFORMATION: Synthetic construct

<400> SEQUENCE: 37

Cys Gln Arg Arg Ser Asn Trp Pro Pro Phe Thr Phe
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Synthetic construct

<400> SEQUENCE: 38

Cys Met Gln Ala Leu Gln Thr Pro Trp Thr Phe
1               5                   10

<210> SEQ ID NO 39
<211> LENGTH: 15
<212> TYPE: PRT
<213> ORGANISM: Artificial Sequence
<220> FEATURE:
<223> OTHER INFORMATION: Synthetic construct

<400> SEQUENCE: 39

Cys Thr Arg Gly Gly Trp Pro Ser Gly Asp Thr Phe Asp Ile Trp
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: Synthetic construct

<400> SEQUENCE: 40

Cys Ala Arg Glu Gly Gly Trp Tyr Ser Val Gly Trp Val Asp Pro Trp
1               5                   10                  15

<210> SEQ ID NO 41
<211> LENGTH: 17
<212> TYPE: PRT
<213> ORGANISM: Artificial Sequence
<220> FEATURE:
<223> OTHER INFORMATION: Synthetic construct

<400> SEQUENCE: 41

Cys Ala Arg Asp Arg Arg Ile Ile Gly Tyr Tyr Phe Gly Met Asp Val
1               5                   10                  15

Trp
```

```
<210> SEQ ID NO 42
<211> LENGTH: 14
<212> TYPE: PRT
<213> ORGANISM: Artificial Sequence
<220> FEATURE:
<223> OTHER INFORMATION: Synthetic construct

<400> SEQUENCE: 42

Cys Ala Arg Leu Leu Ile Glu His Asp Ala Phe Asp Ile Trp
1               5                   10

<210> SEQ ID NO 43
<211> LENGTH: 15
<212> TYPE: PRT
<213> ORGANISM: Artificial Sequence
<220> FEATURE:
<223> OTHER INFORMATION: Synthetic construct

<400> SEQUENCE: 43

Cys Ala Arg Glu Glu Gly Ser Gly Trp Trp Lys His Asp Tyr Trp
1               5                   10                  15

<210> SEQ ID NO 44
<211> LENGTH: 17
<212> TYPE: PRT
<213> ORGANISM: Artificial Sequence
<220> FEATURE:
<223> OTHER INFORMATION: Synthetic construct

<400> SEQUENCE: 44

Cys Val Arg Asp Arg Arg Ile Val Gly Tyr Tyr Phe Gly Leu Asp Val
1               5                   10                  15

Trp

<210> SEQ ID NO 45
<211> LENGTH: 23
<212> TYPE: PRT
<213> ORGANISM: Artificial Sequence
<220> FEATURE:
<223> OTHER INFORMATION: Synthetic construct

<400> SEQUENCE: 45

Cys Ala Lys Asp Ala Phe Tyr Tyr Gly Ser Gly Ser His Phe Tyr Tyr
1               5                   10                  15

Tyr Tyr Tyr Met Asp Val Trp
            20

<210> SEQ ID NO 46
<211> LENGTH: 17
<212> TYPE: PRT
<213> ORGANISM: Artificial Sequence
<220> FEATURE:
<223> OTHER INFORMATION: Synthetic construct

<400> SEQUENCE: 46

Cys Ala Arg Asp Arg Arg Gly Gly Gly Trp Thr Ala Ser Phe Asp Phe
1               5                   10                  15

Trp

<210> SEQ ID NO 47
<211> LENGTH: 15
<212> TYPE: PRT
<213> ORGANISM: Artificial Sequence
<220> FEATURE:
<223> OTHER INFORMATION: Synthetic construct
```

```
<400> SEQUENCE: 47

Cys Ala Arg Gly Gly Trp Pro Ser Gly Asp Thr Phe Asp Ile Trp
1               5                   10                  15

<210> SEQ ID NO 48
<211> LENGTH: 13
<212> TYPE: PRT
<213> ORGANISM: Artificial Sequence
<220> FEATURE:
<223> OTHER INFORMATION: Synthetic construct

<400> SEQUENCE: 48

Cys Ala His His Thr Val Pro Thr Ile Tyr Asp Tyr Trp
1               5                   10

<210> SEQ ID NO 49
<211> LENGTH: 24
<212> TYPE: PRT
<213> ORGANISM: Artificial Sequence
<220> FEATURE:
<223> OTHER INFORMATION: Synthetic construct

<400> SEQUENCE: 49

Cys Ala Lys Asp Ile Gly Arg Tyr Asp His Tyr Asn Ile Phe Gly Arg
1               5                   10                  15

Val Gly Gly Ala Phe Asp Ile Trp
            20

<210> SEQ ID NO 50
<211> LENGTH: 10
<212> TYPE: PRT
<213> ORGANISM: Artificial Sequence
<220> FEATURE:
<223> OTHER INFORMATION: Synthetic construct

<400> SEQUENCE: 50

Cys Gln Gln Tyr Gly Ser Ser Arg Thr Phe
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthetic construct

<400> SEQUENCE: 51

Cys Cys Pro Tyr Ala Asp Thr Trp Val Phe
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic construct

<400> SEQUENCE: 52

Cys Met Gln Ala Leu His Phe Pro Tyr Thr Phe
1               5                   10

<210> SEQ ID NO 53
<211> LENGTH: 11
<212> TYPE: PRT
<213> ORGANISM: Artificial Sequence
```

```
<220> FEATURE:
<223> OTHER INFORMATION: Synthetic construct

<400> SEQUENCE: 53

Cys Gln Gln Leu Ser Gly Tyr Pro Tyr Thr Phe
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Synthetic construct

<400> SEQUENCE: 54

Cys Cys Ser Tyr Ala Thr Thr Trp Val Phe
1               5                   10

<210> SEQ ID NO 55
<211> LENGTH: 10
<212> TYPE: PRT
<213> ORGANISM: Artificial Sequence
<220> FEATURE:
<223> OTHER INFORMATION: Synthetic construct

<400> SEQUENCE: 55

Cys Gln Gln Tyr Gly Ser Ser Pro Thr Phe
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Synthetic construct

<400> SEQUENCE: 56

Cys Gln Gln His Tyr Ser Thr Pro Gly Tyr Thr Phe
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Synthetic construct

<400> SEQUENCE: 57

Cys Gln Gln Leu Asn Ser Tyr Pro Glu Ile Thr Phe
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Synthetic construct

<400> SEQUENCE: 58

Cys Ser Ser Tyr Ala Gly Ser Asn Pro Leu Val Phe
1               5                   10

<210> SEQ ID NO 59
<211> LENGTH: 10
<212> TYPE: PRT
<213> ORGANISM: Artificial Sequence
<220> FEATURE:
```

```
<223> OTHER INFORMATION: Synthetic construct

<400> SEQUENCE: 59

Cys Gln His Tyr Asp Asn Leu Pro Arg Phe
1               5                   10
```

METHODS FOR IDENTIFICATION OF LIGAND-BLOCKING ANTIBODIES AND FOR DETERMINING ANTIBODY POTENCY

CROSS REFERENCE TO RELATED APPLICATIONS

This application is a United States National Phase Patent Application of International Patent Application Number PCT/US2021/014514 filed Jul. 22, 2021, which claims the benefit of U.S. Provisional Patent Application Ser. No. 62/965,257 filed Jan. 24, 2020, the disclosures of which are expressly incorporated herein by reference.

STATEMENT REGARDING FEDERALLY SPONSORED RESEARCH

This invention was made with government support under Grant No. R01 AI131722 awarded by the National Institutes of Health. The government has certain rights in the invention.

FIELD

The present disclosure relates to high-throughput systems and methods for the detection of ligand-blocking antibodies and for determining antibody potency.

BACKGROUND

The antibody repertoire—the collection of antibodies present in an individual—responds efficiently to invading pathogens due to its exceptional diversity and ability to fine-tune antigen specificity via somatic hypermutation. This antibody repertoire is a rich source of potential therapeutics, but its size makes it difficult to examine more than a small cross-section of the total repertoire. Historically, a variety of approaches have been developed to characterize antigen-specific B cells in human infection and vaccination samples. The methods most frequently used include single-cell sorting with fluorescent antigen baits, screens of immortalized B cells, and B cell culture. However, these methods to couple functional screens with sequences of the variable heavy ($V_H$) and variable light ($V_L$) immunoglobulin genes are low throughput; generally, individual B cells can only be screened against a few antigens simultaneously. What is needed are high-throughput systems and methods for the detection of ligand-blocking antibodies and for determining antibody potency.

SUMMARY

In some aspects, disclosed herein is a method for simultaneous detection of an antigen and an antibody that specifically blocks an interaction between said antigen and a ligand thereof, comprising:
  labeling a plurality of antigens with unique antigen barcodes;
  providing a plurality of barcode-labeled antigens to a population of B-cells to form a mixture;
  allowing the plurality of barcode-labeled antigens to bind to the population of B-cells;
  labeling one or more ligands to one or more antigens in the plurality of antigens with unique ligand barcodes;
  introducing the one or more ligands to the mixture of the plurality of barcode-labeled antigens and the population of B-cells;
  washing unbound antigens from the population of B-cells;
  separating the B-cells into single cell emulsions;
  introducing into each single cell emulsion a unique cell barcode-labeled bead;
  preparing a single cell cDNA library from the single cell emulsions;
  performing PCR amplification reactions to produce a plurality of amplicons, wherein the amplicons comprise: 1) the cell barcode and the antigen barcode, 2) the cell barcode and an antibody sequence, and 3) the cell barcode and the ligand barcode, and wherein each amplicon comprises a unique molecular identifier (UMI);
  sequencing the plurality of amplicons;
  removing a sequence lacking the cell barcode, the UMI, the ligand barcode, or the antigen barcode;
  aligning the antibody sequence to a reference library of immunoglobulin V, D, J and C sequences;
  constructing a first UMI count matrix comprising the cell barcode, the antigen barcode, and the antibody sequence and a second UMI count matrix comprising the cell barcode, the ligand barcode, and the antibody sequence;
  determining a first LIBRA-seq score according to the first UMI count matrix and a second LIBRA-seq score according to second UMI count matrix; and
  determining that the antibody blocks the interaction between the antigen and the ligand if the first LIBRA-seq score is higher in comparison to a first reference level and the second LIBRA-seq score is lower in comparison to a second reference level.

In some embodiments, the barcode-labeled antigens are labeled with a first barcode comprising a DNA sequence or an RNA sequence. In some embodiments, the cell barcode-labeled beads are labeled with a second barcode comprising a DNA sequence or an RNA sequence.

In some embodiments, the antibody sequence comprises an immunoglobulin heavy chain (VDJ) sequence, or an immunoglobulin light chain (VJ) sequence.

In some embodiments, the barcode-labeled antigens comprise an antigen from a pathogen or an animal. In some embodiments, the antigen is not purified. In some embodiments, the antigen from a pathogen comprises an antigen from a virus. In some embodiments, the antigen from a virus comprises an antigen from human immunodeficiency virus (HIV), an antigen from influenza virus, or an antigen from respiratory syncytial virus (RSV).

In some embodiments, the method of any preceding aspect further comprises determining a level of somatic hypermutation of the antibody specifically binding to the antigen.

In some embodiments, the method of any preceding aspect further comprises determining a length of a complementarity-determining region (CDR) of the antibody specifically binding to the antigen.

In some embodiments, the method of any preceding aspect further comprises determining a motif of a CDR of the antibody specifically binding to the antigen. In some embodiments, the CDR is selected from the group consisting of CDRH1, CDRH2, CDRH3, CDRL1, CDRL2, and CDRL3.

In some aspects, disclosed herein is a method for simultaneously screening an antigen and an antibody that specifically binds said antigen, comprising:

generating a plurality of antigens using an antigen display technology, wherein each of the plurality of antigens is linked to a nucleic acid sequence that identifies a particular antigen;

providing the plurality of antigens to a population of B-cells;

allowing the plurality of antigens to bind to the population of B-cells;

washing unbound antigens from the population of B-cells;

separating the B-cells into single cell emulsions;

introducing into each single cell emulsion a unique cell barcode-labeled bead;

preparing a single cell cDNA library from the single cell emulsions;

performing PCR amplification reactions to produce a plurality of amplicons, wherein the amplicons comprise: 1) the cell barcode and the nucleic acid sequence that identifies the particular antigen, and 2) the cell barcode and an antibody sequence, and wherein each amplicon comprises a unique molecular identifier (UMI);

sequencing the plurality of amplicons;

removing a sequence lacking the cell barcode, the UMI, or the nucleic acid sequence that identifies the particular antigen;

aligning the antibody sequence to a reference library of immunoglobulin V, D, J and C sequences;

constructing a UMI count matrix comprising the cell barcode, the nucleic acid sequence that identifies the particular antigen, and the antibody sequence;

determining a LIBRA-seq score;

determining the nucleic acid sequence that identifies the particular antigen; and determining that the antibody specifically binds an antigen if the LIBRA-seq score of the antibody for the antigen is higher than a reference level.

In some embodiments, the antigen display technology comprises a ribosome display technology.

In some aspects, disclosed herein is a method for determining a binding potency of an antibody to an antigen, comprising:

labeling a plurality of antigens with unique antigen barcodes;

providing a plurality of barcode-labeled antigens to a population of B-cells;

allowing the plurality of barcode-labeled antigens to bind to the population of B-cells;

washing unbound antigens from the population of B-cells;

separating the B-cells into single cell emulsions;

introducing into each single cell emulsion a unique cell barcode-labeled bead;

preparing a single cell cDNA library from the single cell emulsions;

performing PCR amplification reactions to produce a plurality of amplicons, wherein the amplicons comprise: 1) the cell barcode and the antigen barcode, and 2) the cell barcode and an antibody sequence, and wherein each amplicon comprises a unique molecular identifier (UMI);

sequencing the plurality of amplicons;

removing a sequence lacking the cell barcode, the UMI, or the antigen barcode;

aligning the antibody sequence to a reference library of immunoglobulin V, D, J and C sequences;

constructing a UMI count matrix comprising the cell barcode, the antigen barcode, and the antibody sequence;

determining a LIBRA-seq score; and determining that the antibody has a high binding potency to the antigen if the LIBRA-seq score of the antibody for the antigen is higher than a reference level.

DESCRIPTION OF DRAWINGS

The accompanying figures, which are incorporated in and constitute a part of this specification, illustrate aspects described below.

FIG. 11A shows using the LIBRA-seq with pre-filtering for antigen bound B cells. An experiment was performed with a three-antigen screening library (BG505, CZA97 and HA) on VRC01 Ramos B cell lines and Fe53 Ramos B cell lines. Cells were mixed with DNA-barcoded antigens labeled with streptavidin-PE and sorted for antigen positivity. These single cell suspensions were processed and sequenced. LIBRA-seq scores for each antigen are shown and each cell is plotted based on these scores. Shown are density plots from low to high. Cells fell into two populations based on their LIBRA-seq scores. FIG. 11B shows VRC01 cells, and cells displayed high LIBRA-seq scores for both BG505 and CZA97.

FIG. 13A shows a schematic depicting the experimental set up—where a titration of oligo-labeled S protein was added to the antigen library and donor PBMCs were used as the cellular input. After incubation, cells with high affinity for the antigen would have many S proteins bound, including those added in low concentrations. FIG. 13B shows, after single cell processing and sequencing, antigen binding can be assessed bioinformatically and which cells have high LIBRA-seq scores for many or all of the Spike antigens included were determined.

FIG. 15A shows schematic depicting the experimental set up—where a titration of oligo-labeled S protein was added to the antigen library along with oligo-labeled ACE2 receptor, and donor PBMCs were used as the cellular input. After incubation, cells with high affinity for the antigen would have many S proteins bound, including those added in low concentrations. Antibodies that can block the receptor-protein interaction would not have ACE2 bound to the spike proteins. Antibodies that do not block the interaction would have ACE2 bound to the spike proteins. FIG. 15 shows, after single cell processing and sequencing, assessment of antigen binding bioinformatically and determination regarding which cells have high LIBRA-seq scores for many or all of the Spike antigens included. Additionally, which cells do or do not have ACE2 bound can be determined. In this example, ACE2 is not bound to spike and therefore has a low LIBRA-seq score, indicating that the antibody is able to block ligand binding.

DETAILED DESCRIPTION

Figure 1:
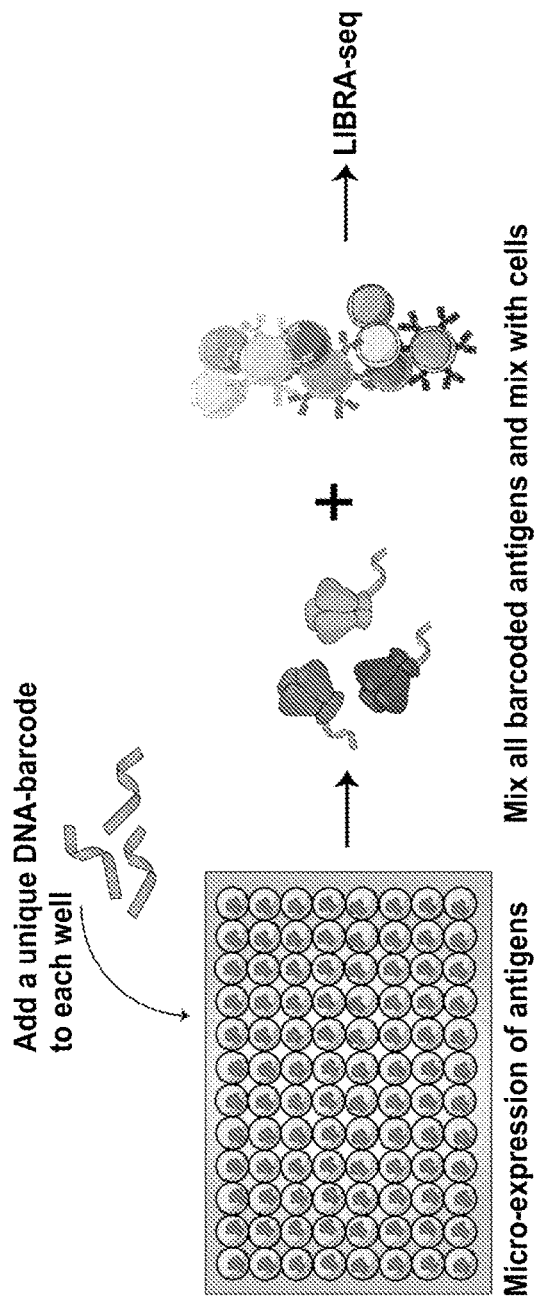
FIG. 1 shows LIBRA-seq for recombinant soluble antigens that are not purified. Microexpression of antigens occurs in a plate format. A unique DNA-barcode is added to each well, and then barcoded antigens are pooled and mixed with cells of interest for LIBRA-seq analysis.
Figure 2:
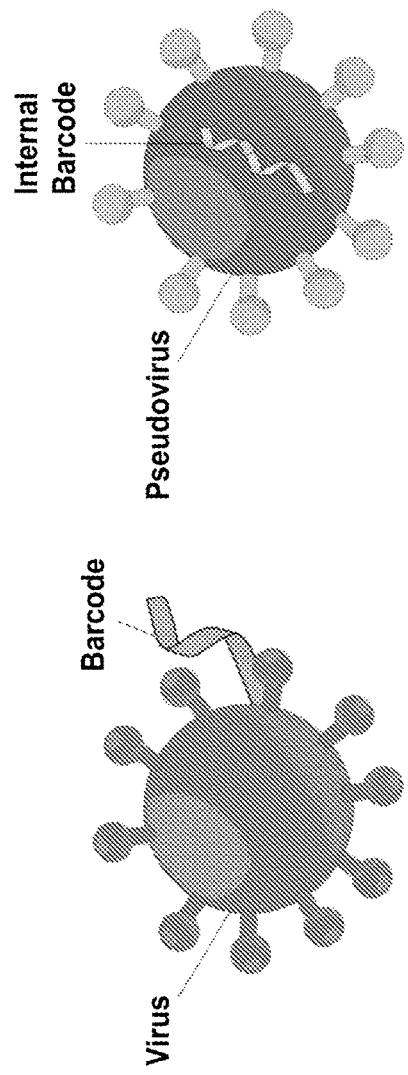
FIG. 2 shows LIBRA-seq for antigens that are not in soluble, recombinant form. The left panel shows that whole virus is tagged with a DNA-barcode and used for LIBRA-seq analysis. The right panel shows that pseudovirus can contain an internal barcode and used for LIBRA-seq analysis.
Figure 3:
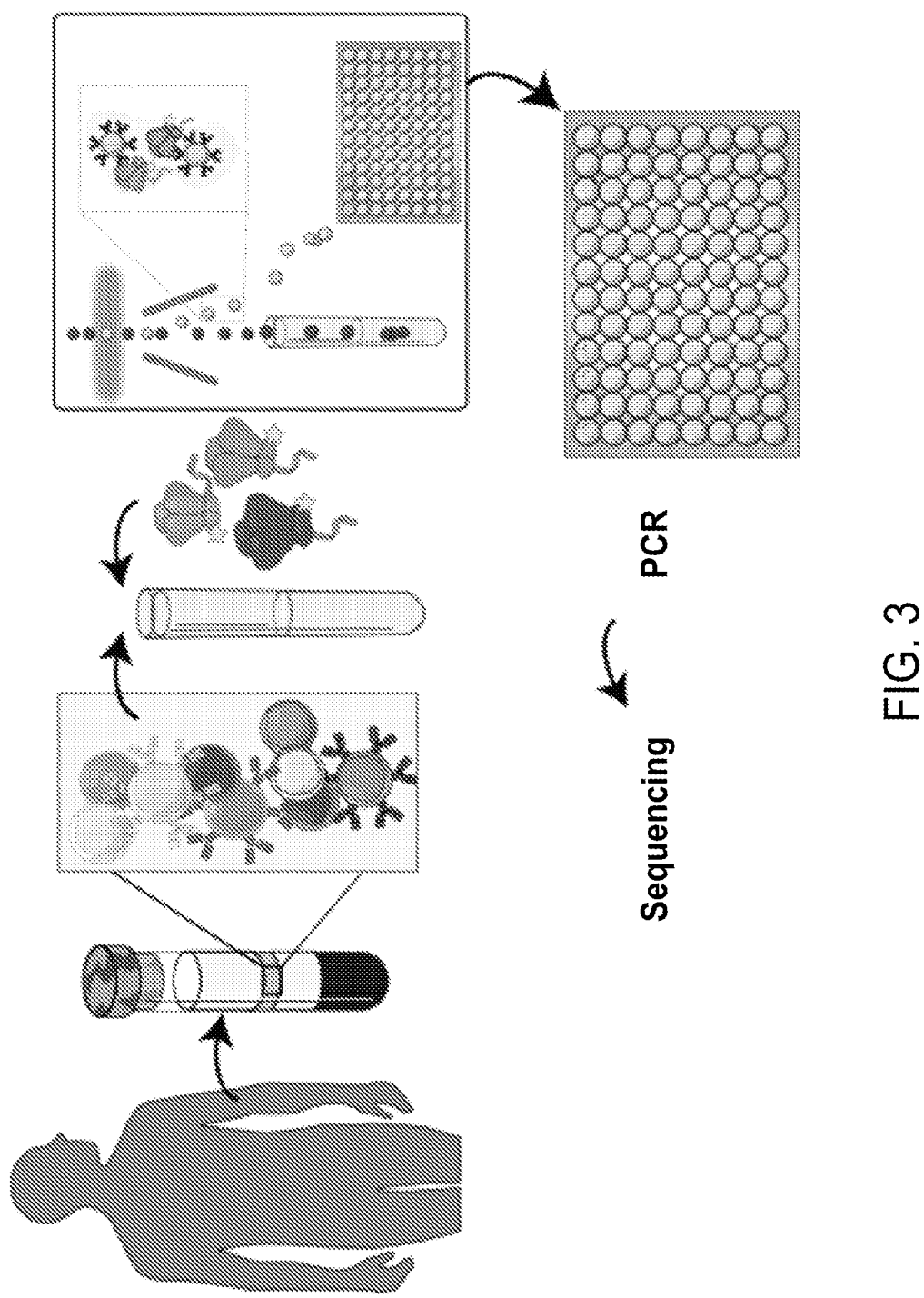
FIG. 3 shows LIBRA-seq in a plate-based single-cell format. Cells of interest are isolated and then mixed with an antigen screening library composed of DNA-barcoded, fluorescently labeled antigens. Antigen-positive cells are single cell sorted by fluorescence activated cell sorting into individual wells of a plate. Cells are lysed and B cell receptor heavy and light chain variable genes along with antigen-oligo sequences are amplified by PCR using primers containing plate and well specific primers. Amplicons are pooled and sequenced.
Figure 4:
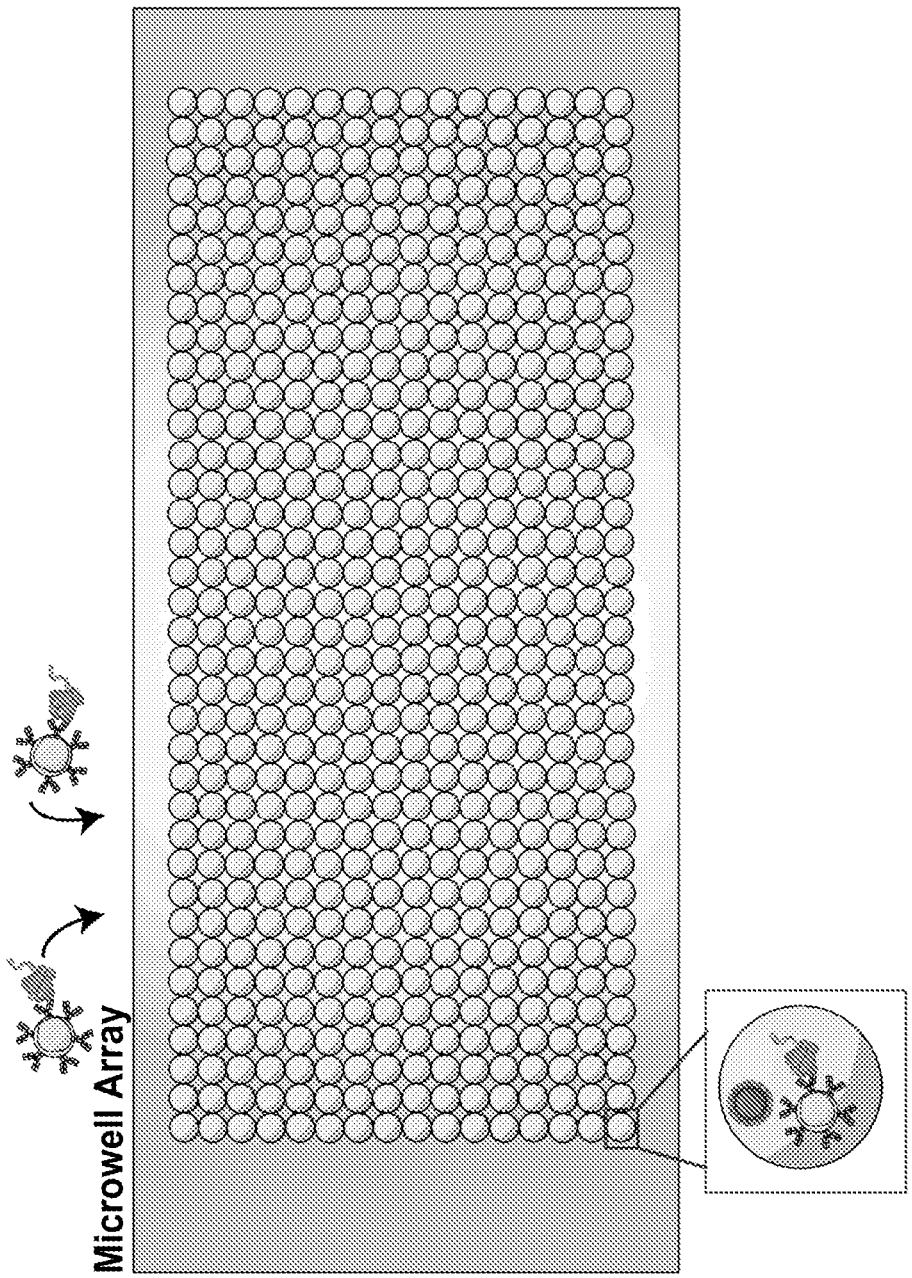
FIG. 4 shows LIBRA-seq in microwell format. After staining cells with an antigen library of DNA-barcoded, fluorescently labeled antigens, antigen positive cells are sorted using fluorescence activated cell sorting. Single cells are deposited into individual, isolated microwells containing reagents and primer beads on a microwell array through gravity and LIBRA-seq is carried out.

Disclosed herein are high-throughput systems and methods for the detection of ligand-blocking antibodies and for determining antibody potency.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed. As used in this disclosure and in the appended claims, the singular forms "a", "an", "the", include plural referents unless the context clearly dictates otherwise.

The following definitions are provided for the full understanding of terms used in this specification.

Terminology

The term "about" as used herein when referring to a measurable value such as an amount, a percentage, and the like, is meant to encompass variations of ±20%, ±10%, ±5%, or ±1% from the measurable value.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

As used herein, the term "subject" or "host" can refer to living organisms such as mammals, including, but not limited to humans, livestock, dogs, cats, and other mammals. Administration of the therapeutic agents can be carried out at dosages and for periods of time effective for treatment of a subject. In some embodiments, the subject is a human.

"Nucleotide," "nucleoside," "nucleotide residue," and "nucleoside residue," as used herein, can mean a deoxyribonucleotide or ribonucleotide residue, or other similar nucleoside analogue. A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate). There are many varieties of these types of molecules available in the art and available herein.

The term "polynucleotide" refers to a single or double stranded polymer composed of nucleotide monomers.

The method and the system disclosed here including the use of primers, which are capable of interacting with the disclosed nucleic acids, such as the antigen barcode as disclosed herein. In certain embodiments the primers are used to support DNA amplification reactions. Typically, the primers will be capable of being extended in a sequence specific manner Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner Typically, the disclosed primers hybridize with the disclosed nucleic acids or region of the nucleic acids or they hybridize with the complement of the nucleic acids or complement of a region of the nucleic acids.

The term "amplification" refers to the production of one or more copies of a genetic fragment or target sequence, specifically the "amplicon". As it refers to the product of an amplification reaction, amplicon is used interchangeably with common laboratory terms, such as "PCR product."

The term "polypeptide" refers to a compound made up of a single chain of D- or L-amino acids or a mixture of D- and L-amino acids joined by peptide bonds.

As used herein, the term "antigen" refers to a molecule that is capable of stimulating an immune response such as by production of antibodies specific for the antigen. Antigens of the present invention can be, for example, an antigen from human immunodeficiency virus (HIV), an antigen from influenza virus, or an antigen from respiratory syncytial virus (RSV). Antigens of the present invention can also be, for example, a human antigen (e.g. an oncogene-encoded protein).

The term "antibodies" is used herein in a broad sense and includes both polyclonal and monoclonal antibodies. In addition to intact immunoglobulin molecules, also included in the term "antibodies" are fragments or polymers of those immunoglobulin molecules, and human or humanized versions of immunoglobulin molecules or fragments thereof, as long as they are chosen for their ability to specifically interact with the HIV virus, such that the HIV viral infection is prevented, inhibited, reduced, or delayed. The antibodies can be tested for their desired activity using the in vitro assays described herein, or by analogous methods, after which their in vivo therapeutic and/or prophylactic activities are tested according to known clinical testing methods. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

Each antibody molecule is made up of the protein products of two genes, heavy-chain gene and light-chain gene. The heavy-chain gene is constructed through somatic recombination of V, D, and J gene segments. In human, there are 51 VH, 27 DH, 6 JH, 9 CH gene segments on human chromosome 14. The light-chain gene is constructed through somatic recombination of V and J gene segments. There are 40 Vκ, 31 Vλ, 5 Jκ, 4 Jλ gene segments on human chromosome 14 (80 VJ). The heavy-chain constant domains that correspond to the different classes of immunoglobulins are called α, δ, ε, γ, and μ, respectively. The "light chains" of antibodies from any vertebrate species can be assigned to one of two clearly distinct types, called kappa (κ) and lambda (λ), based on the amino acid sequences of their constant domains.

The term "monoclonal antibody" as used herein refers to an antibody obtained from a substantially homogeneous population of antibodies, i.e., the individual antibodies within the population are identical except for possible naturally occurring mutations that may be present in a small subset of the antibody molecules. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, as long as they exhibit the desired antagonistic activity.

The disclosed monoclonal antibodies can be made using any procedure which produces monoclonal antibodies. For example, disclosed monoclonal antibodies can be prepared using hybridoma methods, such as those described by Kohler and Milstein, Nature, 256:495 (1975). In a hybridoma method, a mouse or other appropriate host animal is typically immunized with an immunizing agent to elicit lymphocytes that produce or are capable of producing antibodies that will specifically bind to the immunizing agent. Alternatively, the lymphocytes may be immunized in vitro.

The monoclonal antibodies may also be made by recombinant DNA methods. DNA encoding the disclosed monoclonal antibodies can be readily isolated and sequenced using conventional procedures (e.g., by using oligonucleotide probes that are capable of binding specifically to genes encoding the heavy and light chains of murine antibodies). Libraries of antibodies or active antibody fragments can also be generated and screened using phage display techniques, e.g., as described in U.S. Pat. No. 5,804,440 to Burton et al. and U.S. Pat. No. 6,096,441 to Barbas et al.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994 and U.S. Pat. No. 4,342,566. Papain digestion of antibodies typically produces two identical antigen binding fragments, called Fab fragments, each with a single antigen binding site, and a residual Fc fragment. Pepsin treatment yields a fragment that has two antigen combining sites and is still capable of cross linking antigen.

As used herein, the term "antibody or antigen binding fragment thereof" or "antibody or fragments thereof" encompasses chimeric antibodies and hybrid antibodies, with dual or multiple antigen or epitope specificities, and fragments, such as F(ab')2, Fab', Fab, Fv, sFv, scFv and the like, including hybrid fragments. Thus, fragments of the antibodies that retain the ability to bind their specific antigens are provided. Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Also included within the meaning of "antibody or antigen binding fragment thereof" are conjugates of antibody fragments and antigen binding proteins (single chain antibodies). Also included within the meaning of "antibody or antigen binding fragment thereof" are immunoglobulin single variable domains, such as for example a nanobody.

The fragments, whether attached to other sequences or not, can also include insertions, deletions, substitutions, or other selected modifications of particular regions or specific amino acids residues, provided the activity of the antibody or antibody fragment is not significantly altered or impaired compared to the non-modified antibody or antibody fragment. These modifications can provide for some additional property, such as to remove/add amino acids capable of disulfide bonding, to increase its bio-longevity, to alter its secretory characteristics, etc. In any case, the antibody or antibody fragment must possess a bioactive property, such as specific binding to its cognate antigen. Functional or active regions of the antibody or antibody fragment may be identified by mutagenesis of a specific region of the protein, followed by expression and testing of the expressed polypeptide. Such methods are readily apparent to a skilled practitioner in the art and can include site-specific mutagenesis of the nucleic acid encoding the antibody or antibody fragment. (Zoller, M. J. Curr. Opin. Biotechnol. 3:348-354, 1992).

As used herein, the term "antibody" or "antibodies" can also refer to a human antibody and/or a humanized antibody.

Many non-human antibodies (e.g., those derived from mice, rats, or rabbits) are naturally antigenic in humans, and thus can give rise to undesirable immune responses when administered to humans. Therefore, the use of human or humanized antibodies in the methods serves to lessen the chance that an antibody administered to a human will evoke an undesirable immune response.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein, the term "ligand" refers to a biomolecule or a chemical entity having a capacity or affinity for binding to a target. A ligand can include many organic molecules that can be produced by a living organism or synthesized, for example, a protein or portion thereof, a peptide, a polysaccharide, an oligosaccharide, a sugar, a glycoprotein, a lipid, a phospholipid, a polynucleotide or portion thereof, an oligonucleotide, an aptamer, a nucleotide, a nucleoside, DNA, RNA, a DNA/RNA chimera, an antibody or fragment thereof, a receptor or a fragment thereof, a receptor ligand, a nucleic acid-protein fusion, a hapten, a nucleic acid, a virus or a portion thereof, an enzyme, a co-factor, a cytokine, a chemokine, as well as small molecules (e.g., a chemical compound), for example, primary metabolites, secondary metabolites, and other biological or chemical molecules that are capable of activating, inhibiting, or modulating a biochemical pathway or process, and/or any other affinity agent, among others. A ligand can come from many sources, including libraries, such as small molecule libraries, phage display libraries, aptamer libraries, or any other library as would be apparent to one of ordinary skill in the art after review of the disclosure of the present disclosure. In some embodiments, the target is an antigen.

In the present invention, "specific for" and "specificity" means a condition where one of the molecules involved in selective binding. Accordingly, an antibody or a ligand that is specific for one antigen selectively binds that antigen and does not substantially recognize or bind other antigens.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific, in another example, an antibody that specifically binds to an antigen may also bind to different allelic forms of the antigen, However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

"Pharmaceutically acceptable" component can refer to a component that is not biologically or otherwise undesirable, i.e., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents.

The terms "purify" and "purifying" as used herein refers to isolation from a biological sample, i.e., blood, plasma, tissues, exosomes, pathogens, or cells. As used herein the term "purified," when used in the context of, e.g., an antigen, an antibody, a polypeptide, or a nucleic acid, refers to an antigen, an antibody, a polypeptide, or a nucleic acid of interest that is at least 60% free, at least 75% free, at least 90% free, at least 95% free, at least 98% free, and even at least 99% free from other components with which the antigen, the antibody, the polypeptide, the nucleic acid is associated with prior to purification. In some embodiments, an antigen that is not purified refers to said antigen still being associated and/or attached to a biological sample.

As used herein, the terms "treating" or "treatment" of a subject includes the administration of a drug to a subject with the purpose of curing, healing, alleviating, relieving, altering, remedying, ameliorating, improving, stabilizing or affecting a disease or disorder, or a symptom of a disease or disorder. The terms "treating" and "treatment" can also refer to reduction in severity and/or frequency of symptoms, elimination of symptoms and/or underlying cause, and improvement or remediation of damage.

"Therapeutically effective amount" or "therapeutically effective dose" of a composition refers to an amount that is effective to achieve a desired therapeutic result. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as coughing relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

Methods

In some aspects, disclosed herein is a method for simultaneous detection of an antigen and an antibody that specifically blocks an interaction between said antigen and a ligand thereof, comprising:
labeling a plurality of antigens with unique antigen barcodes;
providing a plurality of barcode-labeled antigens to a population of B-cells to form a mixture;
allowing the plurality of barcode-labeled antigens to bind to the population of B-cells;
labeling one or more ligands to one or more antigens in the plurality of antigens with unique ligand barcodes;
introducing the one or more ligands to the mixture of the plurality of barcode-labeled antigens and the population of B-cells;
washing unbound antigens from the population of B-cells;
separating the B-cells into single cell emulsions;
introducing into each single cell emulsion a unique cell barcode-labeled bead;
preparing a single cell cDNA library from the single cell emulsions;
performing PCR amplification reactions to produce a plurality of amplicons, wherein the amplicons comprise: 1) the cell barcode and the antigen barcode, 2) the cell barcode and an antibody sequence, and 3) the cell barcode and the ligand barcode, and wherein each amplicon comprises a unique molecular identifier (UMI);
sequencing the plurality of amplicons;
removing a sequence lacking the cell barcode, the UMI, the ligand barcode, or the antigen barcode;
aligning the antibody sequence to a reference library of immunoglobulin V, D, J and C sequences;
constructing a first UMI count matrix comprising the cell barcode, the antigen barcode, and the antibody sequence and a second UMI count matrix comprising the cell barcode, the ligand barcode, and the antibody sequence;
determining a first LIBRA-seq score according to the first UMI count matrix and a second LIBRA-seq score according to second UMI count matrix; and
determining that the antibody blocks the interaction between the antigen and the ligand if the first LIBRA-seq score is higher in comparison to a first reference level and the second LIBRA-seq score is lower in comparison to a second reference level.

In some embodiments, the first reference level is equal to the second reference level. In some embodiments, the first reference level is about 10%, 20%, 30%, 40%, 50%, 60%, 70%, or 90% higher, or at least 2 times, 3 times, 4 times, 5 times, 6 times, 7 times, 8 times, 9 times, 10 times, 20 times, 40 times, 80 times, 100 times, 500 times higher than the second reference level.

Accordingly, in some embodiments, the method of any preceding aspect further comprises determining a level of somatic hypermutation of the antibody specifically binding to the antigen.

In some embodiments, the method of any preceding aspect further comprises determining a length of a complementarity-determining region (CDR) of the antibody specifically binding to the antigen. The term "complementarity determining region (CDR)" used herein refers to an amino acid sequence of an antibody variable region of a heavy chain or light chain. CDRs are necessary for antigen binding and determine the specificity of an antibody. Each variable region typically has three CDRs identified as CDR1 (CDRH1 or CDRL1, where "H" indicates the heavy chain CDR1 and "L" indicates the light chain CDR1), CDR2 (CDRH2 or CDRL2), and CDR3 (CDRH3 or CDRL3). The CDRs may provide contact residues that play a major role in the binding of antibodies to antigens or epitopes. Four framework regions, which have more highly conserved amino acid sequences than the CDRs, separate the CDR regions in the VH or VL.

Accordingly, in some embodiments, the method of any preceding aspect further comprises determining a motif of a CDR of the antibody specifically binding to the antigen. In some embodiments, the CDR is selected from the group consisting of CDRH1, CDRH2, CDRH3, CDRL1, CDRL2, and CDRL3.

In some embodiments, the method of any preceding aspect further comprises identification of IGHV, IGHD, IGHJ, IGKV, IGKJ, IGLV, or IGLJ genes, or combinations thereof, associated with any particular combination of antigen specificities.

In some embodiments, the method of any preceding aspect further comprises identification of mutations in heavy or light FW1, FW2, FW3 or FW4 associated with any particular combination of antigen specificities.

In some embodiments, the method of any preceding aspect further comprises identification of overall gene expression profiles or select up- or down-regulated genes associated with any particular combination of antigen specificities.

In some embodiments, the method of any preceding aspect further comprises identification of surface markers, via, for example, fluorescence-activated cell sorting, or oligo-conjugated antibodies associated with any particular combination of antigen specificities In some embodiments, the method of any preceding aspect further comprises identification of any combination of BCR sequence feature (for example, immunoglobulin gene, sequence motif, or CDR length), gene expression profile, or surface marker profile associated with any particular combination of antigen specificities.

In some embodiments, the method of any preceding aspect further comprises training a machine learning algorithm on sequence features, sequence motifs, or encoded sequence properties (such as via Kidera factors), associated with any particular combination of antigen specificities for subsequent application to sequenced antibodies lacking antigen specificity information due to not using LIBRA-seq or otherwise.

In some embodiments, the barcode-labeled antigens are labeled with a first barcode comprising a DNA sequence or an RNA sequence. In some embodiments, the cell barcode-labeled beads are labeled with a second barcode comprising a DNA sequence or an RNA sequence.

It should be understood that the barcode described above is conjugated to the barcode-labeled antigen in a way that are known to one of ordinary skill in the art. Conjugates can be chemically linked to the nucleotide or nucleotide analogs. Such conjugates include but are not limited to lipid moieties such as a cholesterol moiety (Letsinger et al., *Proc. Natl. Acad. Sci. USA,* 1989, 86, 6553-6556), cholic acid (Manoharan et al., *Bioorg. Med. Chem. Let.,* 1994, 4, 1053-1060), a thioether, e.g., hexyl-S-tritylthiol (Manoharan et al., Ann. N.Y. Acad. Sci., 1992, 660, 306-309; Manoharan et al., *Bioorg. Med. Chem. Let.,* 1993, 3, 2765-2770), a thiocholesterol (Oberhauser et al., *Nucl. Acids Res.,* 1992, 20, 533-538), an aliphatic chain, e.g., dodecandiol or undecyl residues (Saison-Behmoaras et al., *EMBO J.,* 1991, 10, 1111-1118; Kabanov et al., *FEBS Lett.,* 1990, 259, 327-330; Svinarchuk et al., *Biochimie,* 1993, 75, 49-54), a phospholipid, e.g., di-hexadecyl-rac-glycerol or triethylammonium 1,2-di-O-hexadecyl-rac-glycero-3-H-phosphonate (Manoharan et al., Tetrahedron Lett., 1995, 36, 3651-3654; Shea et al., *Nucl. Acids Res.,* 1990, 18, 3777-3783), a polyamine or a polyethylene glycol chain (Manoharan et al., *Nucleosides & Nucleotides,* 1995, 14, 969-973), or adamantane acetic acid (Manoharan et al., *Tetrahedron Lett.,* 1995, 36, 3651-3654), a palmityl moiety (Mishra et al., *Biochim. Biophys. Acta,* 1995, 1264, 229-237), or an octadecylamine or hexylamino-carbonyl-oxycholesterol moiety (Crooke et al., *J. Pharmacol. Exp. Ther.,* 1996, 277, 923-937. An oligonucleotide barcode can also be conjugated to an antigen using the Solulink Protein-Oligonucleotide Conjugation Kit (TriLink cat no. S-9011) according to manufacturer's instructions. Briefly, the oligo and protein are desalted, and then the amino-oligo is modified with the 4FB crosslinker, and the biotinylated antigen protein is modified with S-HyNic. Then, the 4FB-oligo and the HyNic-antigen are mixed together. This causes a stable bond to form between the protein and the oligonucleotide. In some embodiments, the cell barcode-labeled beads are labeled with a second barcode comprising a DNA sequence or an RNA sequence. In some embodiments, the cell barcode-labeled beads are labeled with a second barcode comprising a DNA sequence. In some embodiments, the cell barcode-labeled beads are labeled with a second barcode comprising an RNA sequence. In some embodiments, the cell barcode-labeled beads are labeled with a barcode on the inside of the bead. In some embodiments, the cell barcode-labeled beads are labeled with a barcode encapsulated within the bead. In some embodiments, the cell barcode-labeled beads are labeled with a barcode on the outside of the bead.

As used herein, "beads" is not limited to a specific type of bead. Rather, a large number of beads are available and are known to one of ordinary skill in the art. A suitable bead may be selected on the basis of the desired end use and suitability for various protocols. In some embodiments, the bead is or comprises a particle or a bead. In some embodiments, the solid support bead is magnetic. Beads comprise particles have been described in the prior art in, for example, U.S. Pat. Nos. 5,084,169, 5,079,155, 473,231, and 8,110,351. The particle or bead size can be optimized for binding B cell in a single cell emulsion and optimized for the subsequent PCR reaction.

These oligos, which contain the cell barcode, both: (1) enable amplification of cellular mRNA transcripts through the template switch oligo that is part of the oligo containing the cell barcode, and (2) directly anneal to the antigen barcode-containing oligos from the antigen. In some embodiments, the oligos delivered from the beads have the general structure: P5_PCR_handle-Cell_barcode-UMI-Template_switch_oligo.

It is noted above that the antibody is determined as specifically binding an antigen if the LIBRA-seq score of the antibody for the antigen is increased in comparison to a control sample. It should be understood herein that between the minimum (y-axis, top) and maximum (y-axis, bottom) LIBRA-seq score for each antigen, the ability of each of 100 cutoffs was tested for its ability to classify each antibody as antigen positive or negative, where antigen positive is defined as having a LIBRA-seq score greater than or equal to the cutoff being evaluated and antigen negative is defined as having a LIBRA-seq score below the cutoff.

In some embodiments, the antibody sequence comprises an immunoglobulin heavy chain (VDJ) sequence, or an immunoglobulin light chain (VJ) sequence. In some embodiments, the antibody sequence comprises an immunoglobulin heavy chain (VDJ) sequence. In some embodiments, the antibody sequence comprises an immunoglobulin light chain (VJ) sequence.

In some embodiments, the barcode-labeled antigens comprise an antigen from a pathogen or an animal. In some embodiments, the barcode-labeled antigens comprise an antigen from a pathogen. In some embodiments, the barcode-labeled antigens comprise an antigen from an animal. In some embodiments, the animal is a mammal, including, but not limited to, primates (e.g., humans and nonhuman primates), cows, sheep, goats, horses, dogs, cats, rabbits, rats, mice and the like. In some embodiments, the subject is a human.

In some embodiments, the antigens are purified before labeling with barcodes. In some embodiments, the antigens are not purified before labeling with barcodes.

Therefore, in some embodiments, the LIBRA-seq disclosed herein can be used for soluble antigens that are not purified. Antigens can be arranged in a plate format for microexpression. Each antigen is expressed in microculture in a single well on a plate. In some embodiments, a unique barcode is added to each well, barcoded antigens are mixed together, mixed with B cells, and LIBRA-seq is performed as described herein.

In some embodiments, the LIBRA-seq disclosed herein can be used for antigens that are not in soluble form. In some embodiments, a whole virus is tagged with one or more barcodes. In some embodiments, a whole virus can use scRNA-seq to exploit the intrinsic diversity within variants of the same virus (e.g., different strains of HIV-1). In some embodiments, a pseudovirus can contain internal barcode for LIBRA-seq. In some embodiments, comprehensive mutant virus libraries can be generated using the methods of (e.g. Dingens et al (2019). An Antigenic Atlas of HIV-1 Escape from Broadly Neutralizing Antibodies Distinguishes Functional and Structural Epitopes. Immunity, 50(2):520-532.e3). In some embodiments, a whole cell can be tagged by lentiviral transfection with barcode or CRISPR-based tagging. In some embodiments, a membrane-anchored antigen (in particular, those for membrane proteins), e.g., the one on liposomes is tagged with one or more barcodes.

Antigens can also be formatted into antigen microarrays (for example, VirScan technology, as described in Xu G J, et al. Comprehensive serological profiling of human populations using a synthetic human virome. Science. 2015; 348 (6239):aaa0698). DNA microarrays can be used followed by phage display of antigens. In some embodiments herein, a unique barcode is added to each antigen in the microarray.

Antigens of the present invention can also be an antigen from a pathogen or an animal. In some embodiments, the antigen is from a human. In some embodiments, the antigen from a human is an antigen encoded by an oncogene. In some embodiments, the antigen encoded by an oncogene can be, for example, NY-ESO-1, MAGEA-A3, hTERT, Tyrosinase, gp100, MART-1, melanA, beta-catenin, CDC27, hsp70, HLA-A2-R170J, CEA, AFP, PSA, EBV-EBNA, HPV16-E7, MUC-1, HER-2/neu, or Mammaglobin-A.

In some embodiments, the antigen from a pathogen comprises an antigen from a virus. In some embodiments, the antigen from a virus comprises an antigen from human immunodeficiency virus (HIV), an antigen from influenza virus, or an antigen from respiratory syncytial virus (RSV).

In some embodiments, the antigen from a virus comprises an antigen from human immunodeficiency virus (HIV). In some embodiments, the antigen from a virus comprises an antigen from influenza virus. In some embodiments, the antigen from a virus comprises an antigen from respiratory syncytial virus (RSV).

In some embodiments, the antigen from HIV comprises an antigen from HIV-1. In some embodiments, the antigen from HIV comprises an antigen from HIV-2. In some embodiments, the antigen from HIV comprises HIV-1 Env. In some embodiments, the antigen from influenza virus comprises hemagglutinin (HA). In some embodiments, the antigen from RSV comprises an RSV F protein. In some embodiments, the antigen is selected from the antigens listed in Table 1.

TABLE 1

Antigen screening library for human B-cell sample analysis. For a set of pathogens, shown are selected protein targets, number of strains, and resulting total number of antigens in the screening library.

| Pathogen | Protein targets | # Strains | # Antigens in library |
| --- | --- | --- | --- |
| CMV | gB | 2 | 2 |
| Dengue | E, prM | 5 | 10 |
| Hepatitis B | HBsAg | 2 | 2 |
| Hepatitis C | E2, E1E2 | 2 | 4 |
| HIV-1 | gp140, gp120, MPER | 3 | 9 |
| HPV | L1 | 3 | 3 |
| HSV-1 | gB | 1 | 1 |
| Influenza | HA, NA | * | 12 |
| Malaria | PfCSP | 1 | 1 |
| Measles | H, F | 1 | 2 |
| Mumps | HN, NP | 1 | 2 |
| Norovirus | P | 10 | 10 |
| Rhinovirus | VP1 | 5 | 5 |
| Rotavirus | VP7, VP4 | ^ | 8 |
| RSV | F, G | 4 | 8 |
| Rubella | E1 | 1 | 1 |
| Staphylococcus aureus | HtsA, SirA, IsdB, SstD | 1 | 4 |
| UPEC | Hma, IutA, FyuA, IreA | 1 | 4 |
| Zika | E, prM | 1 | 2 |

*influenza: A (6 HA, 4 NA) and B (2 HA);
^rotavirus: 6 G, 2 P variants)

In some embodiments, the population of B-cells comprise a memory B-cell, a plasma cell, naïve B cell, an activated B-cell, or a B-cell line. In some embodiments, the population of B-cells comprise a memory B-cell, a plasma cell, a naïve B cell, an activated B-cell, or a B-cell line. In some embodiments, the population of B-cells comprise a plasma cell. In some embodiments, the population of B-cells comprise a naïve B cell. In some embodiments, the population of B-cells comprise an activated B-cell. In some embodiments, the population of B-cells comprise a B-cell line.

In some aspects, disclosed herein is a method for simultaneously screening an antigen and an antibody that specifically binds said antigen, comprising:
generating a plurality of antigens using an antigen display technology, wherein each of the plurality of antigens is linked to a nucleic acid sequence that identifies a particular antigen;
providing the plurality of antigens to a population of B-cells;
allowing the plurality of antigens to bind to the population of B-cells;
washing unbound antigens from the population of B-cells;
separating the B-cells into single cell emulsions;
introducing into each single cell emulsion a unique cell barcode-labeled bead;
preparing a single cell cDNA library from the single cell emulsions;
performing PCR amplification reactions to produce a plurality of amplicons, wherein the amplicons comprise: 1) the cell barcode and the nucleic acid sequence that identifies the particular antigen, and 2) the cell barcode and an antibody sequence, and wherein each amplicon comprises a unique molecular identifier (UMI);
sequencing the plurality of amplicons;
removing a sequence lacking the cell barcode, the UMI, or the nucleic acid sequence that identifies the particular antigen;
aligning the antibody sequence to a reference library of immunoglobulin V, D, J and C sequences;
constructing a UMI count matrix comprising the cell barcode, the nucleic acid sequence that identifies the particular antigen, and the antibody sequence;
determining a LIBRA-seq score;
determining the nucleic acid sequence that identifies the particular antigen; and
determining that the antibody specifically binds an antigen if the LIBRA-seq score of the antibody for the antigen is higher than a reference level.

In some embodiments, the amplicon comprising the cell barcode and nucleic acid sequence that identifies a particular antigen and the amplicon comprising the cell barcode and an antibody sequence are separate amplicons. In some embodiments, the antibody sequence can be a heavy chain sequence and/or a light chain sequence. In some embodiments, the antibody sequence is a heavy chain sequence. In some embodiments, the antibody sequence is a light chain sequence.

In some embodiments, the antigen display technology comprises a ribosome display technology.

In some embodiments, the nucleic acid sequence that identifies a particular antigen is a coding nucleic acid. In some embodiments, the nucleic acid sequence that identifies a particular antigen is a coding nucleic acid sequence that is covalently linked to the antigen. In some embodiments, the nucleic acid sequence that identifies a particular antigen is a nucleic acid sequence from the DNA (for example, viral DNA). In some embodiments, the nucleic acid sequence that identifies a particular antigen is an exon sequence. In some embodiments, the nucleic acid sequence that identifies a particular antigen is a transcript sequence. In some embodiments, the nucleic acid sequence that identifies a particular antigen is an antigen barcode.

In some embodiments, the antigen display technology comprises a phage display technology, a yeast display technology, or a ribosome display technology. In some embodiments, the term "phage display technology," as used herein is meant to refer to those forms described more fully in H. Benjamin Larman, Nat Biotechnol. 2011 June; 29(6): 535-541, and U.S. Pat. No. 6,017,732, incorporated herein by reference for all purposes. In some embodiments, the term "ribosome display technology," as used herein is meant to refer to those forms described more fully in Zhu et al., Nat Biotechnol. 2013 April; 31(4): 331-334, WO2001/75097 and U.S. Pat. No. 774,557, incorporated herein by reference for all purposes. See also, Science. 2015 Jun. 5; 348(6239).

In some embodiments, B cells are purified from a sample of interest (for example, tumor infiltrates); non B cell populations from the sample of interest are obtained (for example, consisting of many tumor cells) to sequence exome; an antigen screening library is made using ribosome display of exons; and B cells are screened against the antigen screening library.

In some aspects, disclosed herein is a method for determining a binding potency of an antibody to an antigen, comprising:
  labeling a plurality of antigens with unique antigen barcodes;
  providing a plurality of barcode-labeled antigens to a population of B-cells;
  allowing the plurality of barcode-labeled antigens to bind to the population of B-cells;
  washing unbound antigens from the population of B-cells;
  separating the B-cells into single cell emulsions;
  introducing into each single cell emulsion a unique cell barcode-labeled bead;
  preparing a single cell cDNA library from the single cell emulsions;
  performing PCR amplification reactions to produce a plurality of amplicons, wherein the amplicons comprise: 1) the cell barcode and the antigen barcode, and 2) the cell barcode and an antibody sequence, and wherein each amplicon comprises a unique molecular identifier (UMI);
  sequencing the plurality of amplicons;
  removing a sequence lacking the cell barcode, the UMI, or the antigen barcode;
  aligning the antibody sequence to a reference library of immunoglobulin V, D, J and C sequences;
  constructing a UMI count matrix comprising the cell barcode, the antigen barcode, and the antibody sequence;
  determining a LIBRA-seq score; and
  determining that the antibody has a high binding potency to the antigen if the LIBRA-seq score of the antibody for the antigen is higher than a reference level.

The term "binding potency" used herein refers to the concentration or amount of an antibody required to produce a certain effect, such as binding to a certain amount of antigen. The antibody-antigen binding potency can be measured using a variety of techniques, for example ELISA, SPR, BLI, etc.

In some embodiments, the methods herein are used for epitope mapping. In some embodiments, the method of any preceding aspect further comprises a step for pre-filtering for antigen-bound B cells.

EXAMPLES

The following examples are set forth below to illustrate the systems, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. LIBRA-seq for Antibody Discovery with Ligand Blocking

Figure 5:
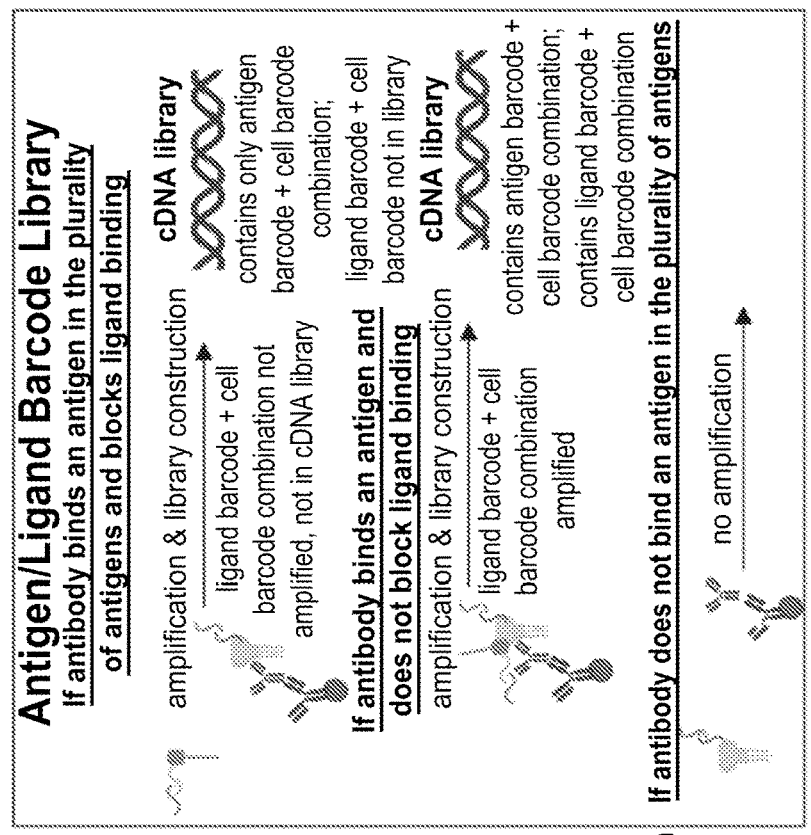
FIG. 5 shows LIBRA-seq for antibody discovery with ligand blocking: for BCRs on a B cell.
Figure 5:
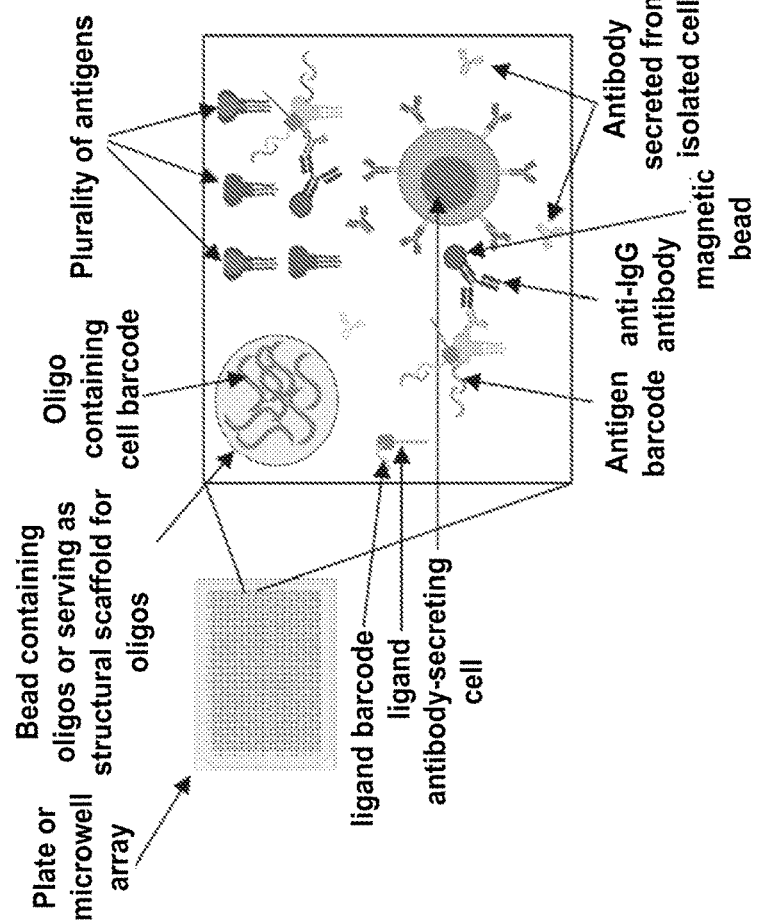
Figure 6:
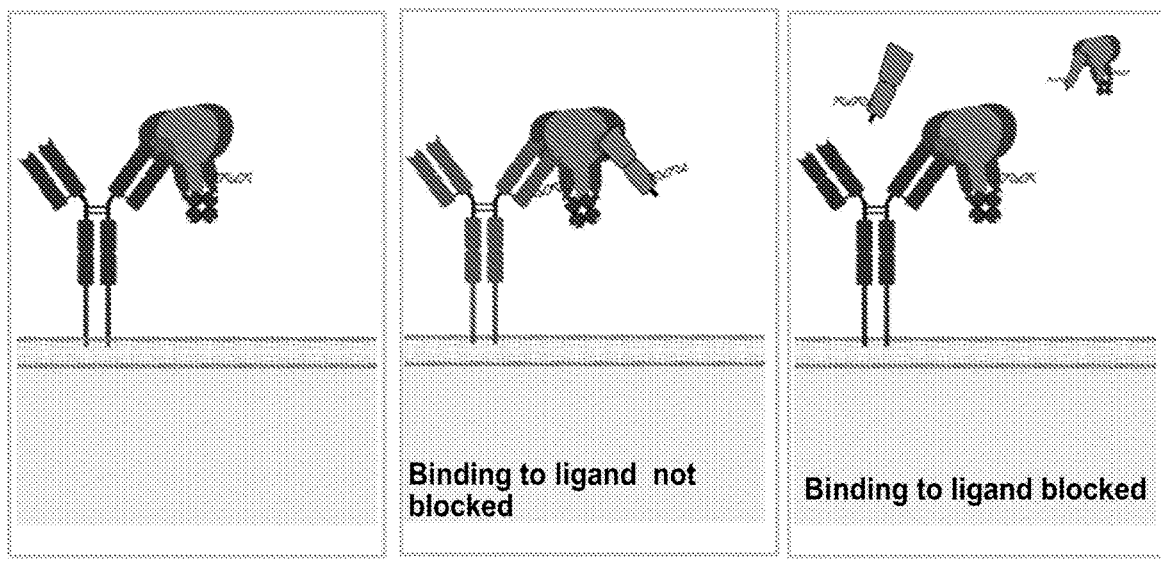
FIG. 6 shows LIBRA-seq for antibody discovery with ligand blocking: for BCRs on a B cell. The left panel shows traditional LIBRA-seq pipeline identifies antigen specificity via sequencing of unique antigen barcodes. Some antibodies function by blocking interactions between a protein antigen and a ligand. To identify antibodies such as these, a barcoded ligand is used as part of the LIBRA-seq antigen panel. Upon sequencing, B cells that have a high LIBRA-seq score for the given antigen but a low LIBRA-seq score for the corresponding ligand may indicate antigen-ligand binding may be decreased when the antigen is bound to the BCRs for the given B cell.

In some antibody discovery efforts, it is important to identify functional (as opposed to binding-only) antibodies, and in many cases the function of interest is the identification of antibodies that can block antigen interactions with its cognate ligand. Rather than performing standard screens for antigen-binding antibodies, followed by ligand-blocking assays for select antibodies, disclosed herein is a method adapting LIBRA-seq to simultaneously obtain information on the ligand-blocking abilities of identified B cells, from the same sequencing experiment. To achieve this, for a given antigen, the known cognate ligand can also be labeled with a unique barcode. B cells are first mixed with the antigens from the screening library, followed by mixing with any ligand(s) (FIG. 5). Upon sequencing, B cells that have a high LIBRA-seq score for the given antigen but a low LIBRA-seq score for the corresponding ligand indicates antigen-ligand binding is decreased when the antigen is bound to the BCRs for the given B cell (FIG. 6).

LIBRA-seq experiments are performed with barcoded ligands and their respective barcoded antigen partners in the screening library, along with B cell lines both for antibodies that do and do not block ligand binding for the same antigen. For example, soluble CD4 is used as a ligand for the HIV-1 Env antigen, along with VRC01 B cells (which can block Env-CD4 binding) and another HIV-1 B cell line (e.g., 2G12, which cannot not block Env-CD4 binding). In these experiments, several parameters are varied and evaluated, including ligand amounts, number of oligos per ligand molecule, barcode variation, ligand-to-antigen ratio, etc. Ultimately, these experiments inform the selection of parameters that optimize the LIBRA-seq ability to accurately identify ligand-blocking antibodies using a benchmarking system of known antigen-ligand and B cell line combinations.

Figure 7:
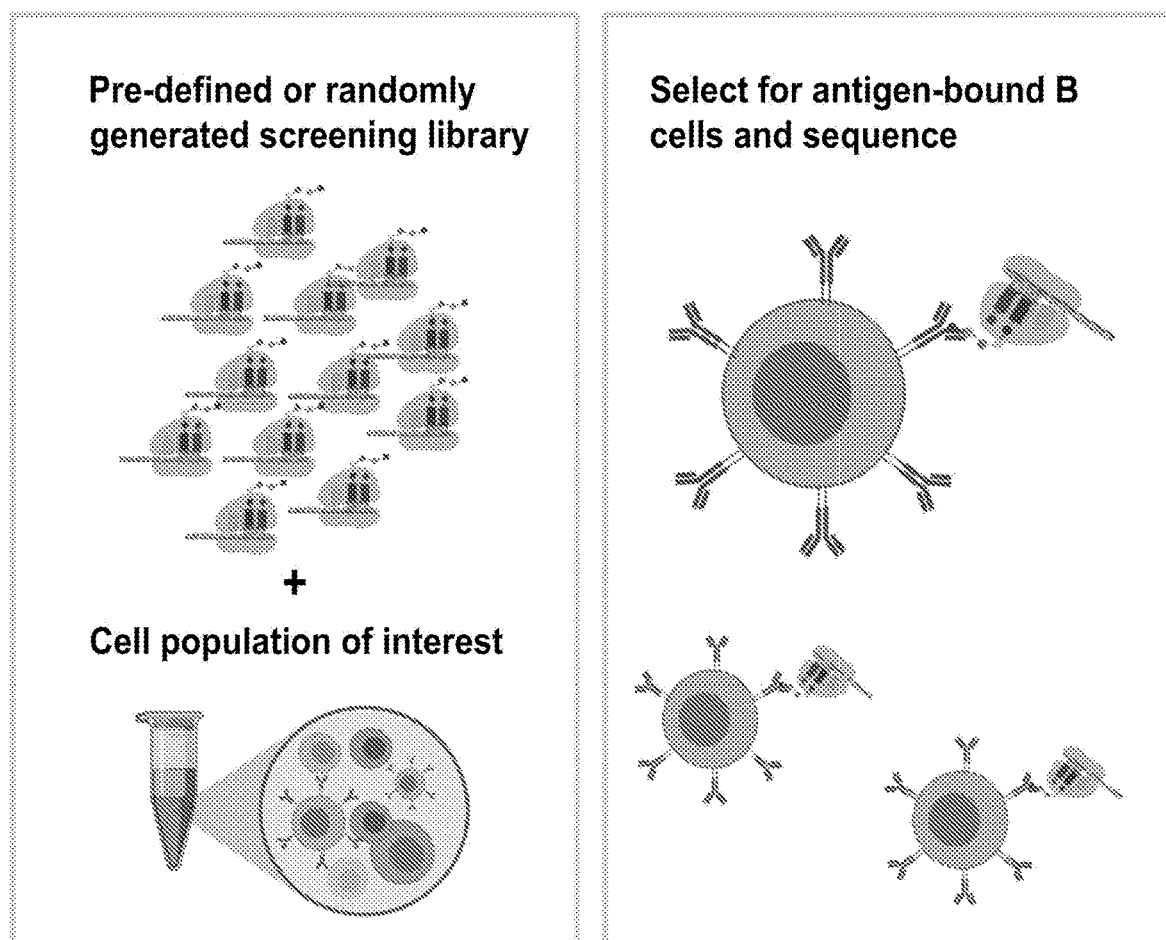
FIG. 7 shows LIBRA-seq for high-throughput antigen screening and de novo antigen discovery. The LIBRA-seq pipeline is conducive to coupling with high-throughput antigen screening methods, such as ribosome display. Predefined or randomly generated screening libraries displayed on ribosomes can be mixed with cell populations of interest and sequenced. In this example, mRNA sequences from each bound ribosome are incorporated with the cellular barcode, along with all other cellular transcripts, for bioinformatic mapping of B cell receptor sequence to displayed open reading frames (ORFs).

Example 2. LIBRA-Seq for High-Throughput Antigen Screening and De Novo Antigen Discovery The typical LIBRA-seq platforms require oligo-tagging of a set of target antigens. LIBRA-seq can be extended to use antigen display technologies (such as phage, yeast, or ribosome display), such that for each given B cell, all bound displayed antigens can be sequenced simultaneously. For example, ribosome display for protein antigens is an established technique (e.g., Zhu et al., Nat Biotechnol. 2013 April; 31(4): 331-334). LIBRA-seq can utilize display technologies by combining with the B cell side of the analysis, resulting in paired BCR sequence-antigen identity information (FIG. 7). In particular, this approach allows sequencing of genetic material for the displayed antigens. For example, with phage display, the phage DNA can be sequenced; for ribosome display, the antigen mRNA is tethered to the antigen protein that it encodes through lack of a stop codon. The advantage of the display technologies is that an immensely larger set of antigens can be screened in a single experiment (tens of thousands to potentially billions), compared to the dozens to hundreds of antigens that are screened with the traditional approach that requires production and purification for each individual antigen. The antigen display library can be targeted (e.g., multiple variants of the same antigen protein) or it can be general (e.g., thousands of human proteins). Importantly, this approach enables antigen discovery: B cells can be screened against large-scale human proteome, virome, microbiome etc. antigen libraries without a pre-conceived notion about the specific antigen target that these B cells can target, thus enabling the simultaneous discovery of both antibodies and antigens.

Example 3. LIBRA-Seq for Antibody-Antigen Potency Determination

One of the primary goals in many antibody discovery efforts is to efficiently select for high-potency as opposed to low-potency antibodies that are specific to a target antigen. It is therefore of value to enable LIBRA-seq to estimate, or at least rank-order, B cell potency for a target antigen. To achieve this, several approaches are disclosed herein.

Figure 8:
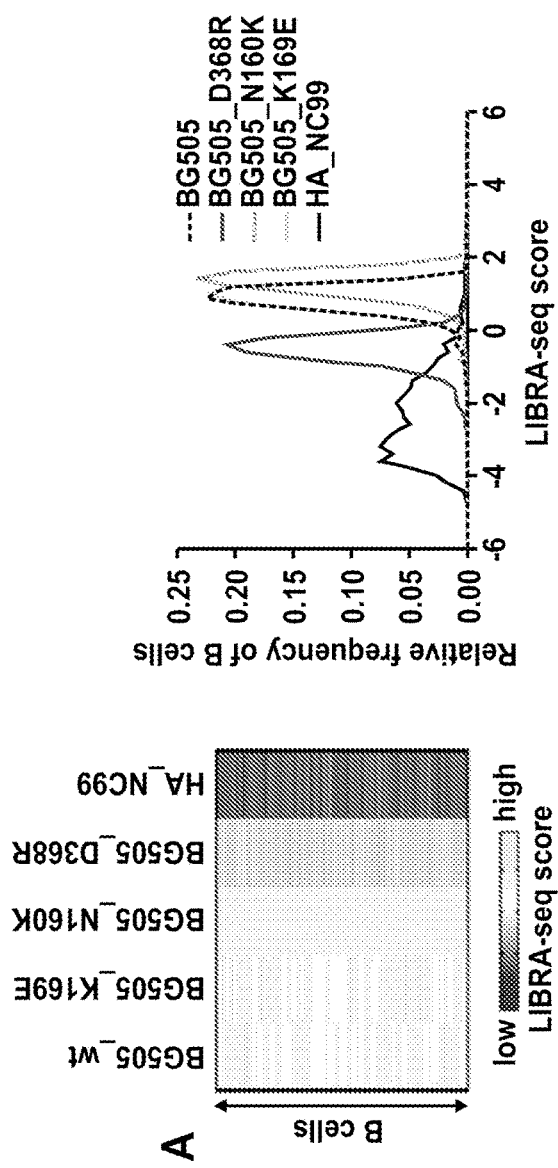
FIG. 8 shows LIBRA-seq for antibody-antigen potency determination—qualitative potency estimates. VRC01 Ramos B cells and Fe53 Ramos B cells were mixed with an antigen screening library composed of BG505 and three epitope mutants of BG505 (N160K, K169E, D358R) and HA. Overall, VRC01 cells showed lower scores for BG505 D368R compared to BG505 wt, BG505 K169E, and BG505 N160K, in agreement with the decrease affinity of VRC01 for the D368R mutant compared to wildtype. These data indicate that LIBRA-seq can be used to make qualitative potency estimates for an antibody and antigen.
Figure 8:
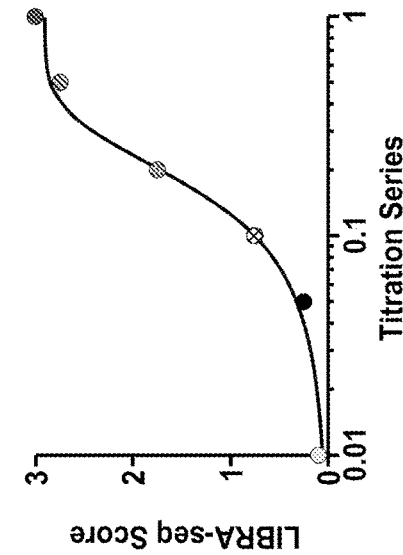

Qualitative potency estimates. For many target antigens of biomedical interest, there already exist antibodies for which potency measurements can be performed using standard techniques, such as biolayer interferometry. To investigate the ability of LIBRA-seq to discriminate B cells based on the potency of the BCRs for a target antigen, LIBRA-seq is evaluated to score B cells that have different affinities for the same antigen. In particular, the LIBRA-seq scores are compared for the different influenza HA antigens from the screening library against the different influenza antibodies represented in the B cell lines, since all of these antibody-antigen pairs have known potency. In addition, B cells expressing the BCRs for a low-potency germline-reverted version of Fe53 are used. These experiments are performed at different B cell ratios, to interrogate the limits of LIBRA-seq detection of antigen-specific B cells as a function of both potency and relative abundance. Upon sequencing, the LIBRA-seq scores for a given antigen are higher for higher-potency B cells and lower for lower-potency B cells. Ultimately, for antigens for which a known antibody exists, the LIBRA-seq experiments can be set up to use a B cell control with known antigen potency, in order to prioritize newly identified B cells based on their LIBRA-seq scores compared to the control. The data in FIG. 8 show lower scores for VRC01 cells against the lower-potency D368R mutation compared to wildtype antigen, indicating that LIBRA-seq scores can be used as a relative indicator of antibody-antigen potency.

Figure 9:
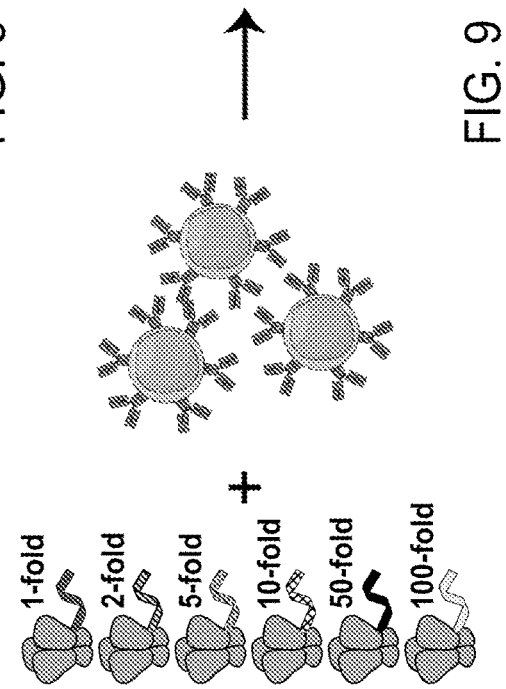
FIG. 9 shows LIBRA-seq for antibody-antigen potency determination—quantitative potency estimates. To quantitatively assess antibody-antigen potency, several aliquots of the same antigen are independently labeled with different unique barcodes and then mixed at different fold dilutions with B cells. Upon performing LIBRA-seq, a pseudo-potency measurement is obtained for the B cells by fitting a curve to the fold-dependent LIBRA-seq scores for the given antigen.

Quantitative potency estimates. The ability of LIBRA-seq for estimating antibody-antigen potency in a more quantitative manner is also explored. To achieve this, a given antigen is aliquoted and barcoded with different unique barcodes (one barcode per aliquot). A titration series are then performed, such that the B cells are be mixed with different (but pre-defined) amounts from each of the barcoded aliquots for the given antigen. Upon sequencing, a pseudo-potency measurement can be obtained for a given B cell by fitting a curve to the LIBRA-seq scores for the different barcoded aliquots for the same antigen (FIG. 9). This experimental setup is used with the different antigens from the screening library discussed above, followed by a comparison of the resulting pseudo-potency measurements for the respective antigen-specific B cell lines to the measured potencies for the respective antibodies. The effect of a number of parameters are evaluated (including the number of unique barcodes per antigen (e.g., between 4 and 10), amounts for each barcoded variant of an antigen, etc.) on LIBRA-seq potency estimation accuracy. This approach allows for comparisons between different antibodies and antigens, and even between multiple LIBRA-seq experiments, without the need for a known antibody-antigen potency control, in order to enable the prioritization of B cells based on the potency estimates for any given target antigen.

Example 4. LIBRA-Seq with Pre-Filtering for Antigen-Bound B Cells

While the LIBRA-seq antigen screening library can be adapted to each specific sequencing experiment, within any given sample, there can be a substantial number of B cells specific to antigens that are not included in the screening library (antigen-specific B cells for a given antigen are typically low frequency). When such B cells are included in the sequencing experiment, only their BCR sequence information is obtained, without any information on their antigen specificity, since there are no matching antigens in the antigen screening library for these B cells.

To address this, strategies are explored for focusing the sequencing specifically toward antigen-bound B cells (for which both antibody sequence and antigen specificity information can be obtained). Namely, antigen-positive cells are sorted, using the following strategies for fluorescently labeling the antigens in the antigen screening library: (a) fluorescently labeled streptavidin and (b) fluorescently labeled oligo barcodes, synthesized by Sigma Aldrich with four internal fluorescein-dTs and a 5' amino C6 linker.

Figures 11A, 11B:
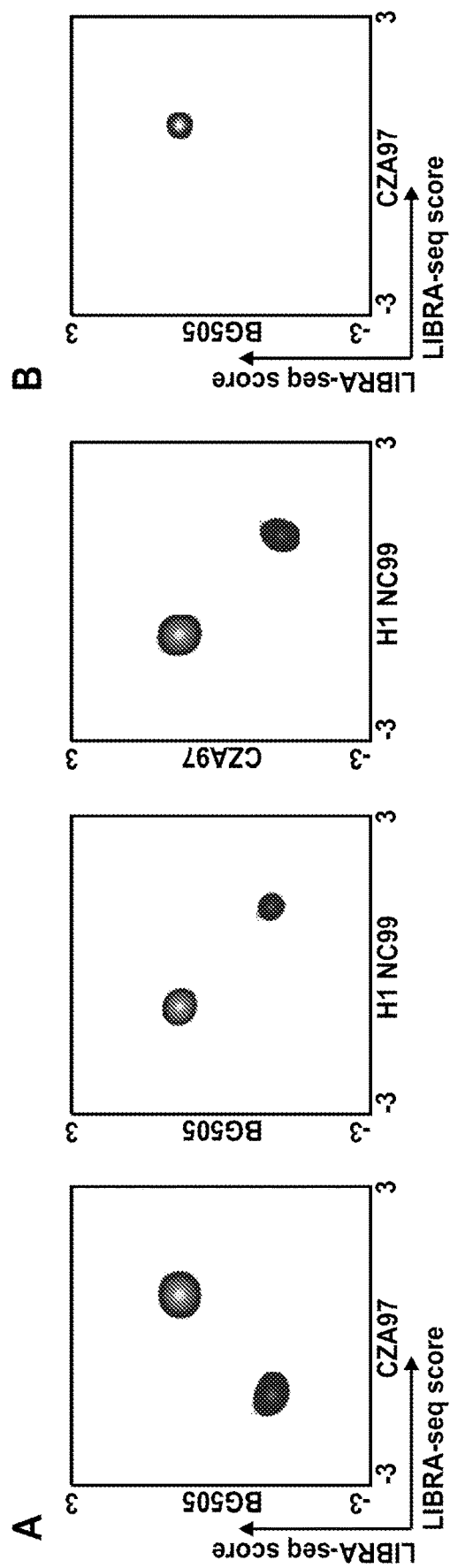
FIGS. 11A and 11B show LIBRA-seq with pre-filtering for antigen-bound B cells.
Figure 12:
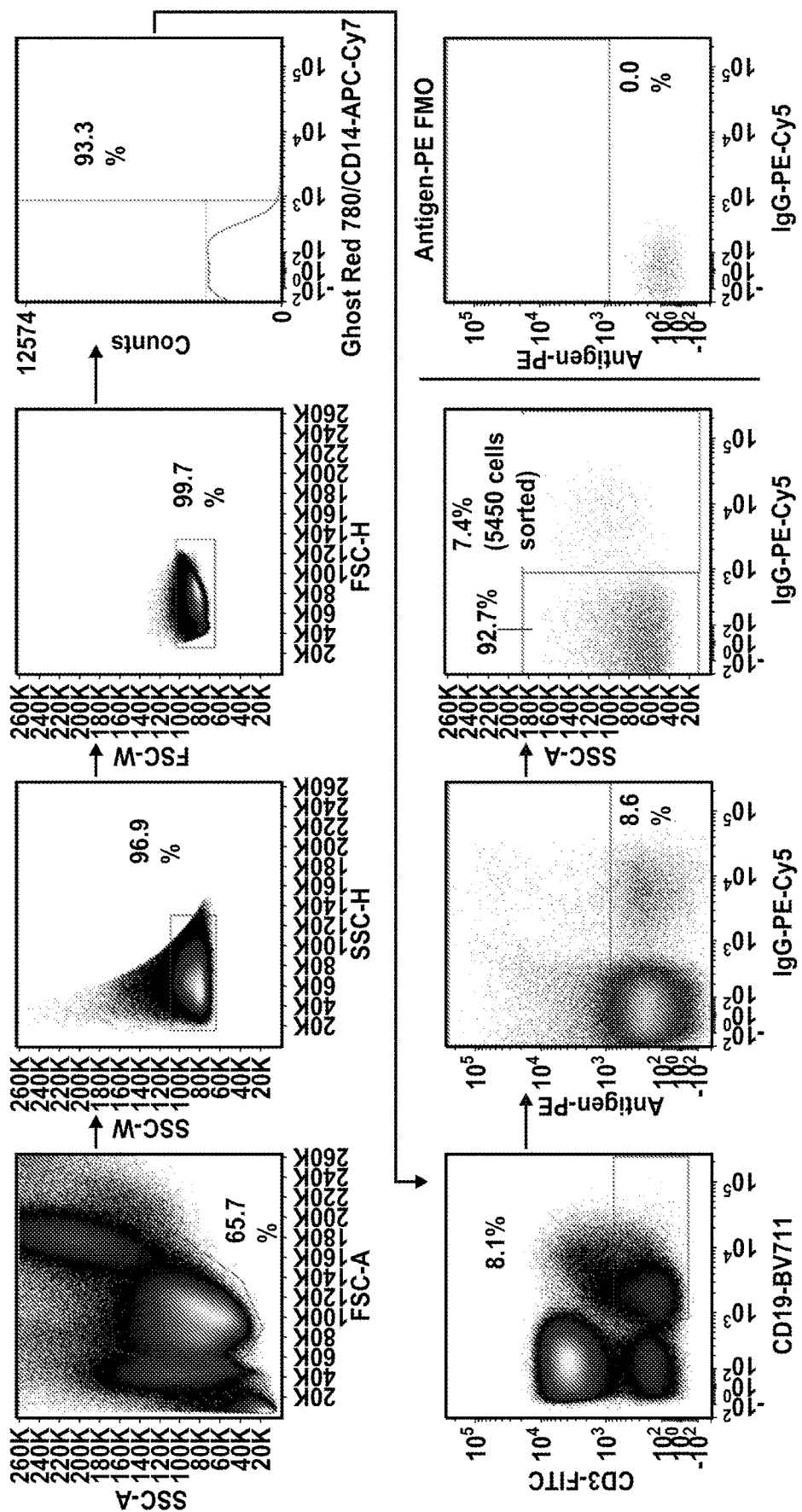
FIG. 12 shows the gating scheme for LIBRA-seq with pre-filtering for antigen bound B cells applied to HIV-infection sample from donor N90. PBMCs from donor N90 were mixed with a nine-antigen screening library composed of HIV trimers and influenza trimers, each labeled with streptavidin PE. Cells were gated on forward scatter and side scatter. Then cells were gated for singlets on side scatter width and height. Cells were further gated for singlets based on forward scatter width and height. Singlets were gated as Live/CD14−/CD3−/CD19+. From the Live/CD14−/CD3−/CD19+ population, antigen positive cells were sorted and enriched for IgG+. An antigen-PE fluorescence minus one control was also included.
Figures 13A, 13B:
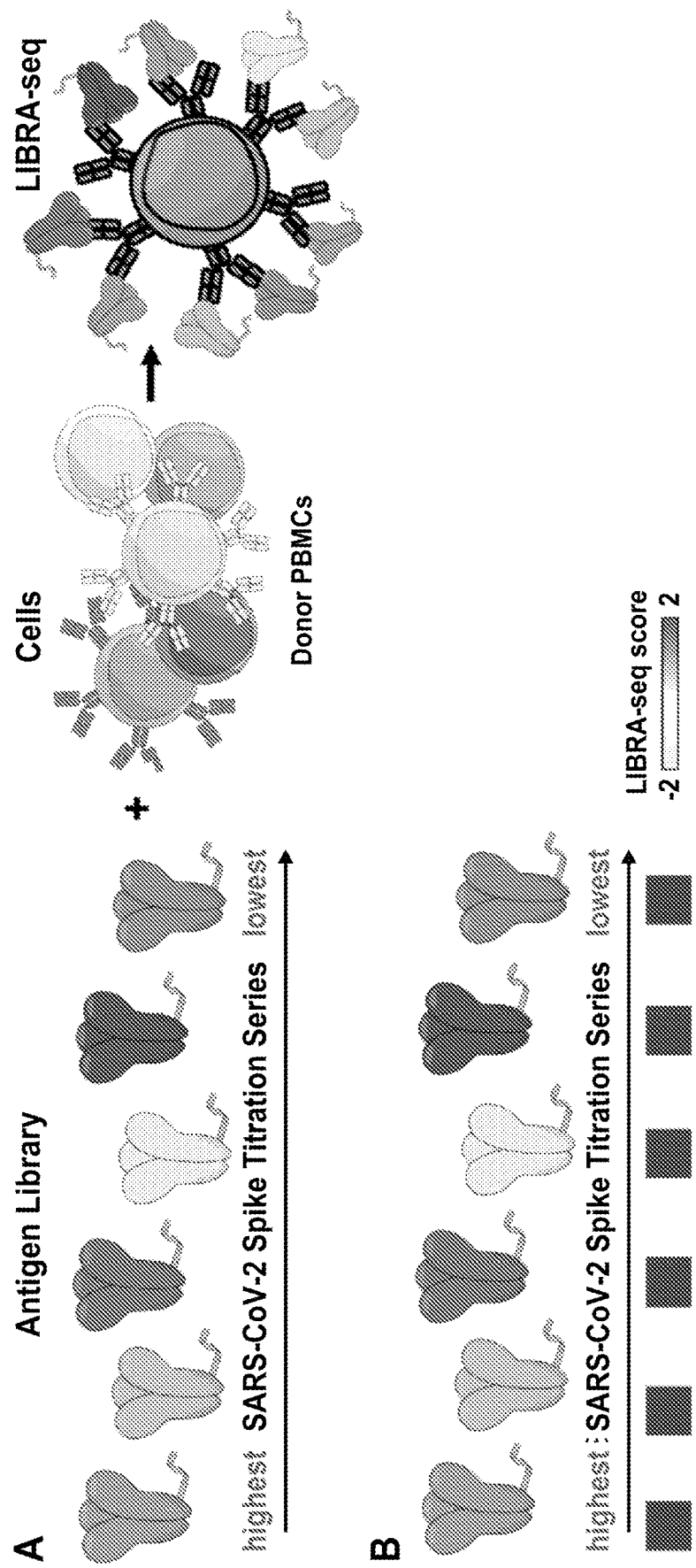
FIGS. 13A-13B show LIBRA-seq antigen titration for identification of potent antibodies. To create affinity-type measurements and identify high potency antibodies using the LIBRA-seq technology, an antigen screening library containing an antigen titration was applied. Six different amounts of oligo-labeled SARS-CoV-2 S protein were included in a screening library. Antibodies with high affinity for SARS-CoV-2 S showed reactivity for S protein added in lower amounts.
Figure 14:
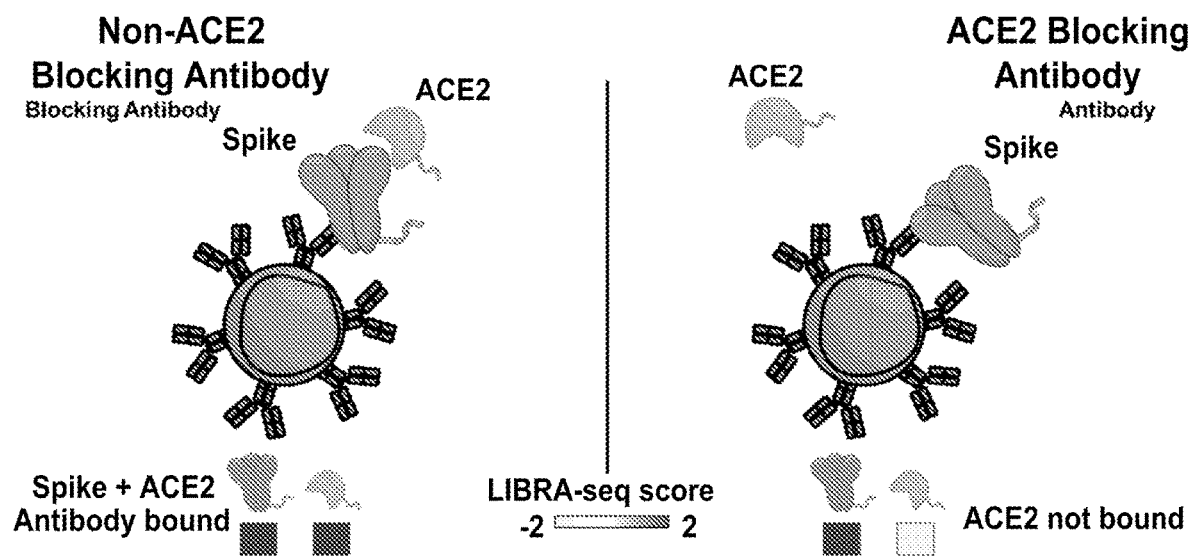
FIG. 14 shows assessment of ligand blocking functionality using LIBRA-seq through identification of ACE2 blocking antibodies. For assessment of ligand blocking functionality using LIBRA-seq, an antigen and its ligand are included in the screening library. If an antibody does not disrupt the interaction between a protein and its receptor, then the LIBRA-seq scores for the protein and the receptor are high (left). If an antibody does block the interaction, then the score for the protein is high and the score for the receptor is low (right). This allows for identification of antibodies that block receptor binding. This can also indicate neutralization potential of the antibodies. This schematic depicts this experimental rationale using SARS-CoV-2 as an example—where oligo labeled spike and oligo-labeled ACE2 (the spike receptor) are included in the antigen screening library.
Figures 15A, 15B:
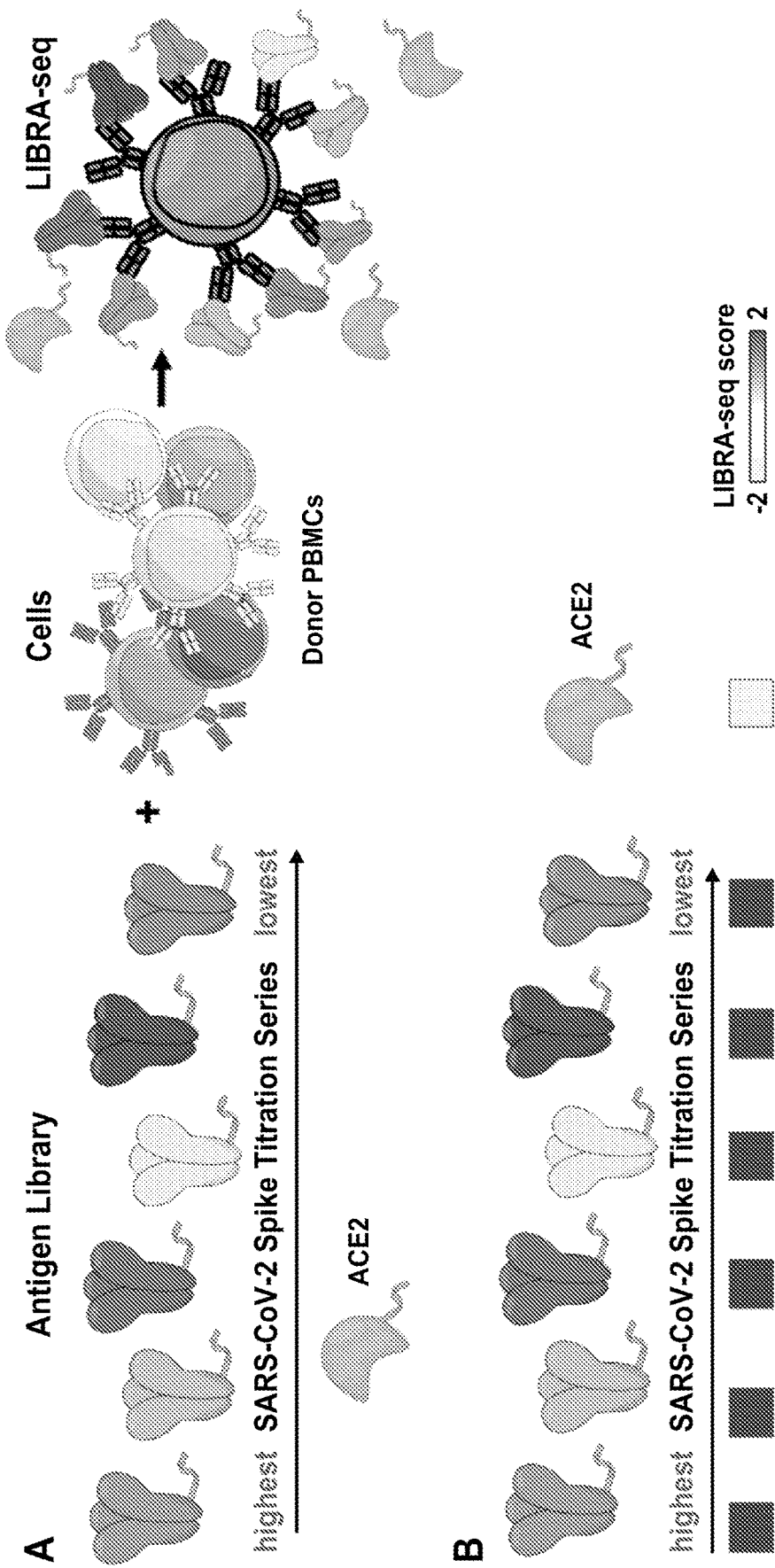
FIGS. 15A-15B show LIBRA-seq antigen titration with ligand blocking for identification of potent antibodies. In this schematic, an antigen titration along with the inclusion of the receptor are included to identify potent antibodies with ligand blocking functionality.
Figure 16:
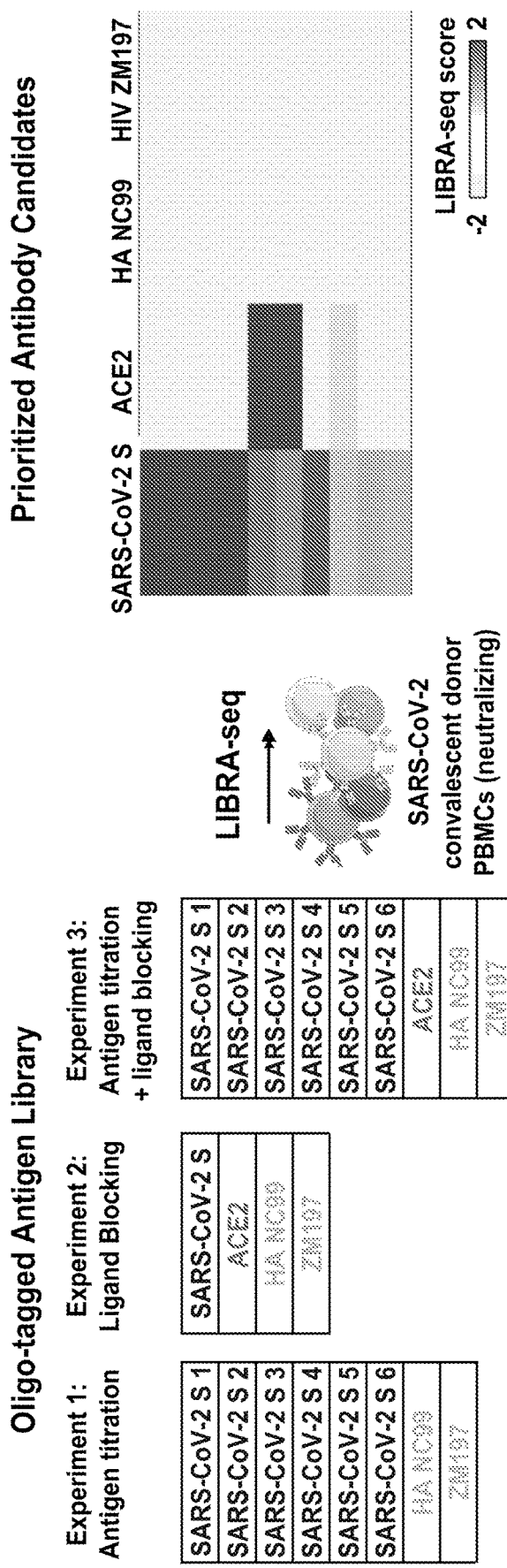
FIG. 16 shows extending LIBRA-seq technology for identification of potent SARS-CoV-2 antibodies. To assess affinity measurements and ligand blocking functionality, three LIBRA-seq experiments were performed. To assess affinity measurements, in experiment 1, the antigen library consisted of an antigen titration of SARS-CoV-2 S protein along with control antigens influenza HA NC99 and HIV ZM197. To assess ligand blocking, in experiment 2, the antigen library consisted of SARS-CoV-2 S protein along with its receptor, ACE2, and control antigens influenza HA NC99 and HIV ZM197. To assess affinity measurements in combination with ligand blocking, in experiment 3, the antigen library consisted of an antigen titration of SARS-CoV-2 S protein, ACE2, and control antigens influenza HA NC99 and HIV ZM197. Each antigen library was incubated with SARS-CoV-2 convalescent donor PBMCs and LIBRA-seq was performed. After single cell processing, next generation sequencing, and bioinformatic analysis, antibody heavy chain and light chain sequence features and antigen LIBRA-seq scores for thousands of cells were assessed. For the antigen titration experiments, antibodies that showed high scores for S protein added in lower amounts were identified. For ligand blocking, antibodies that had high scores for S protein and low scores for ACE2 were identified—showing envelope (gray) which blocks its interaction with CD4 ligand (green). VRC34 (purple, right) recognizes a site on the HIV envelope protein which does not block this interaction.
Figures 17A, 17B, 17C:
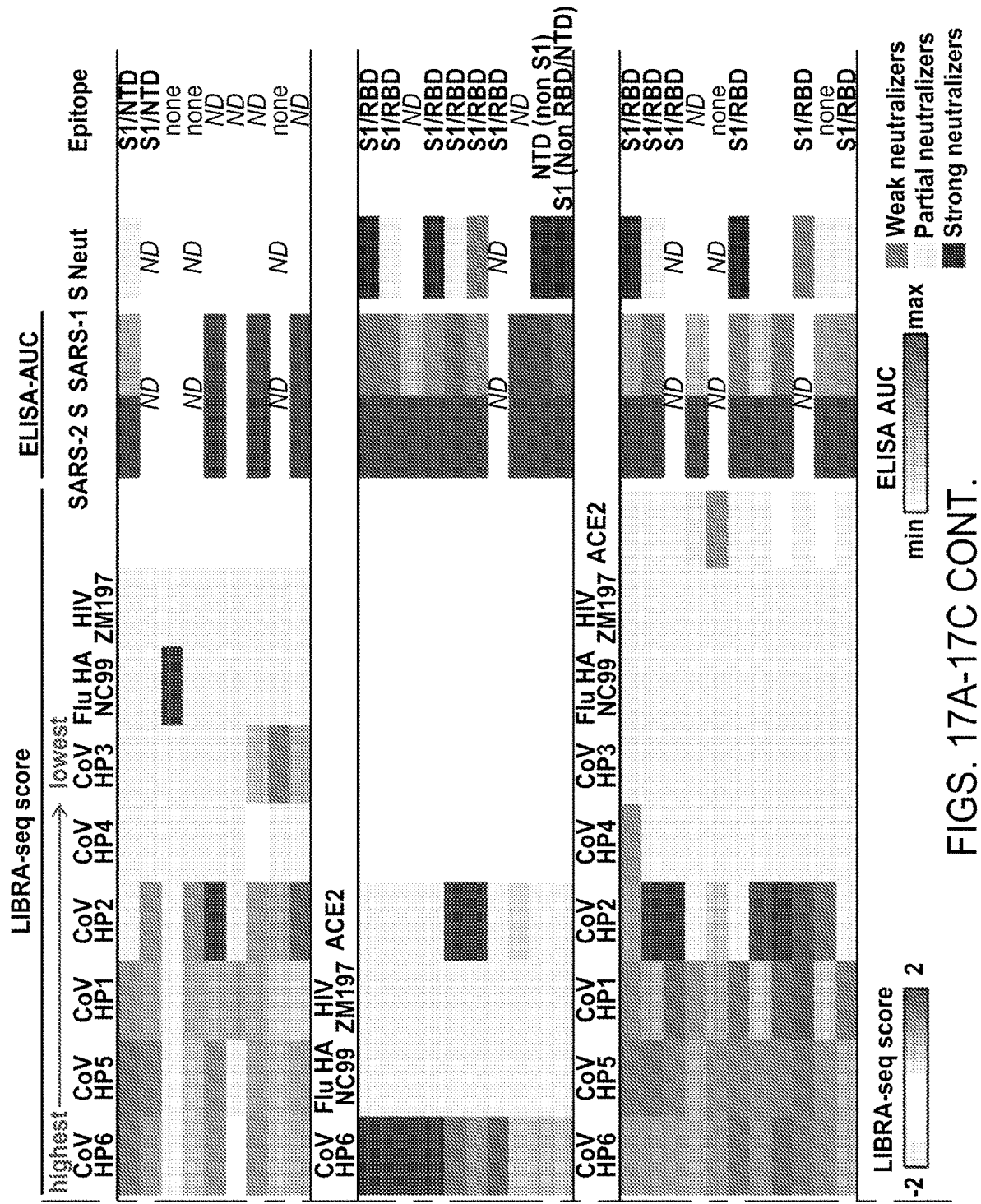
Figure 18A:
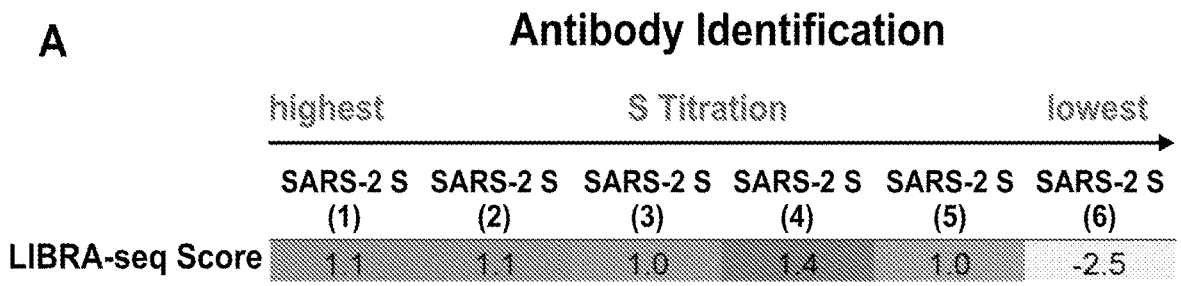
Figure 18B:
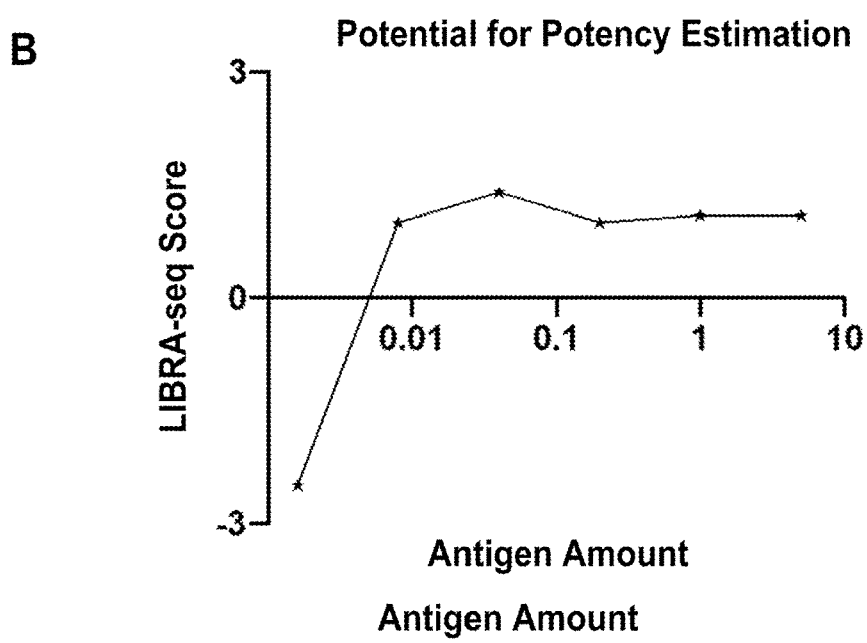
Figure 18C:
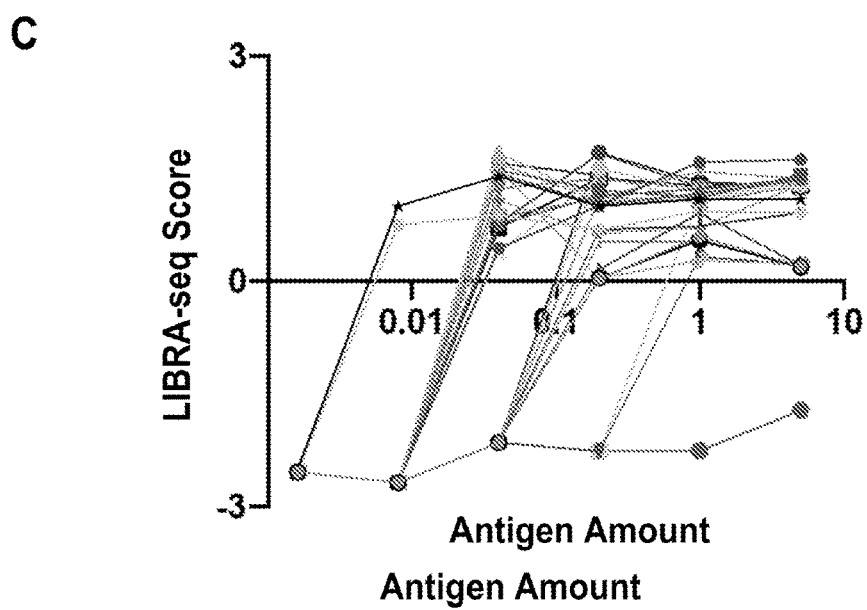
Figure 19:
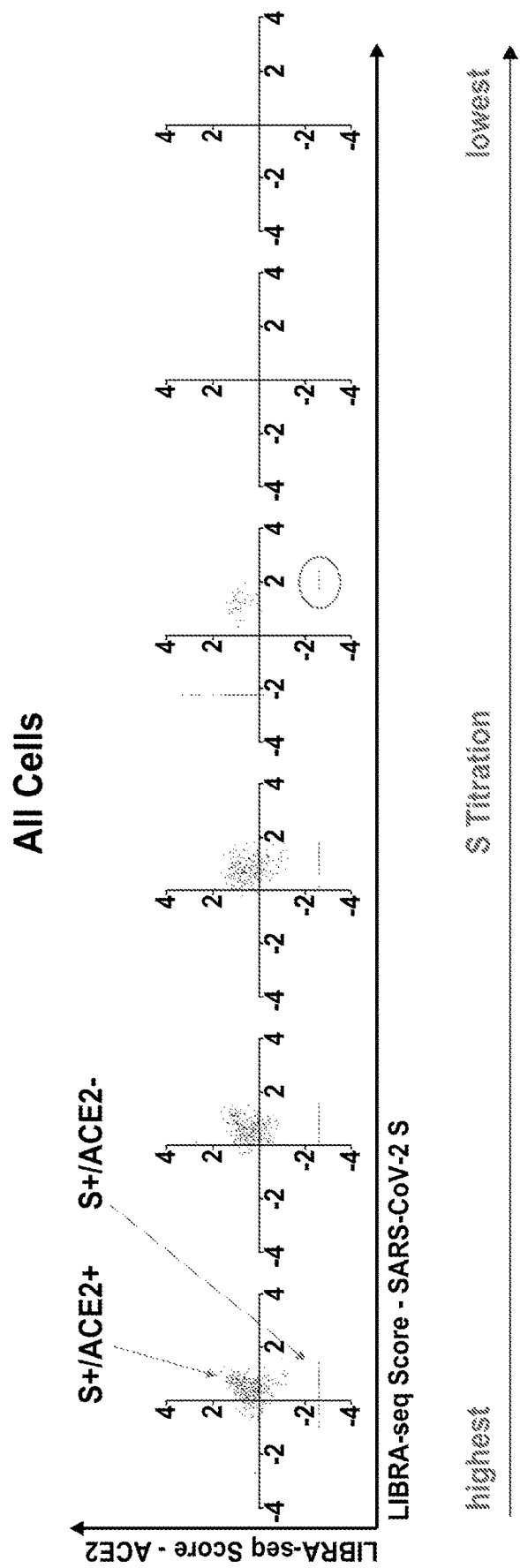
Figure 20A:
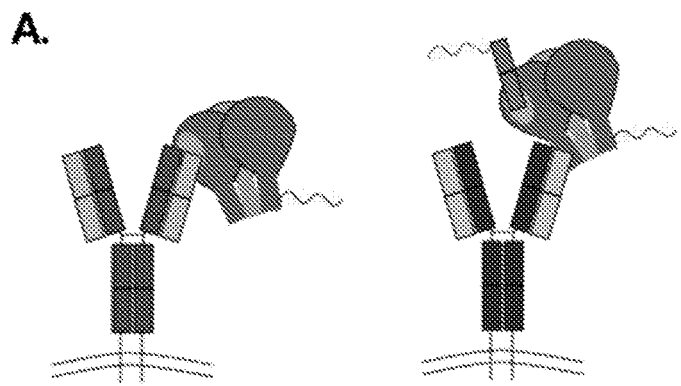
FIGS. 20B-20C show binding of soluble HIV envelope and CD4 proteins to VRC01 and VRC34-expressing Ramos B cells lines measured by flow cytometry. The Influenza-specific FE53 Ramos B cell line is shown as negative control.
Figure 20B:
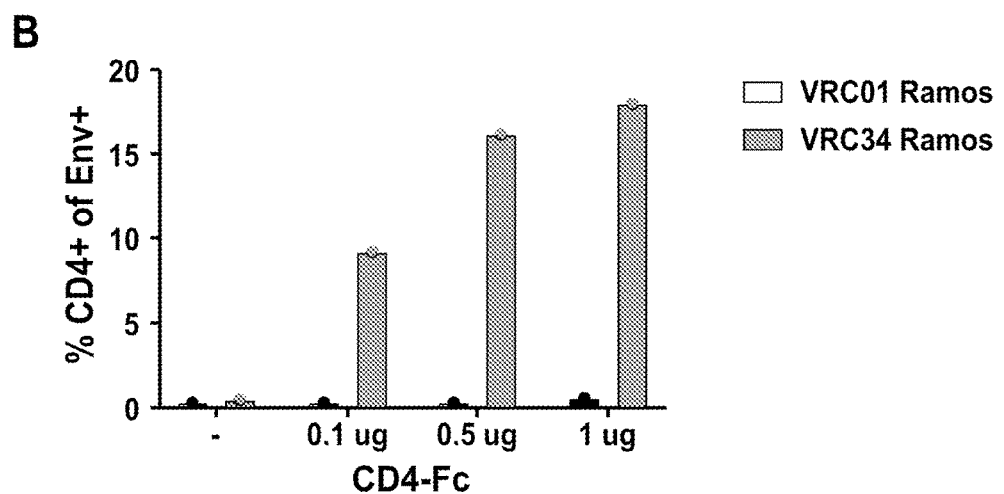
Figure 20C:
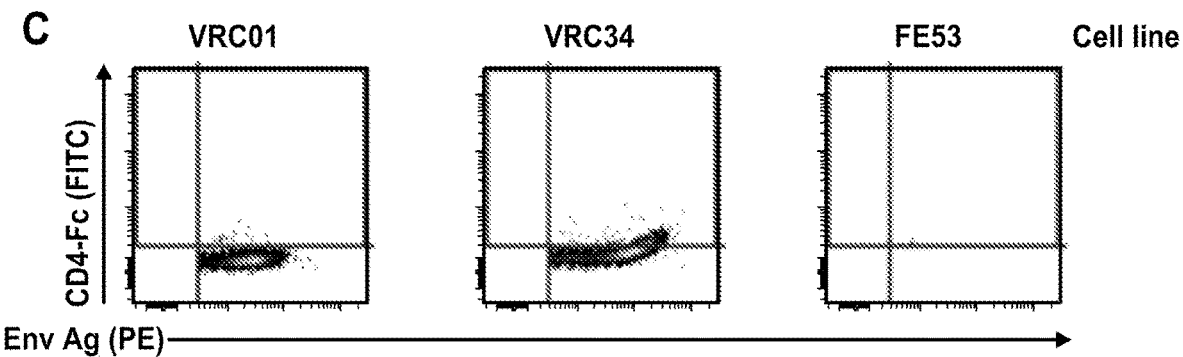
Figure 21:
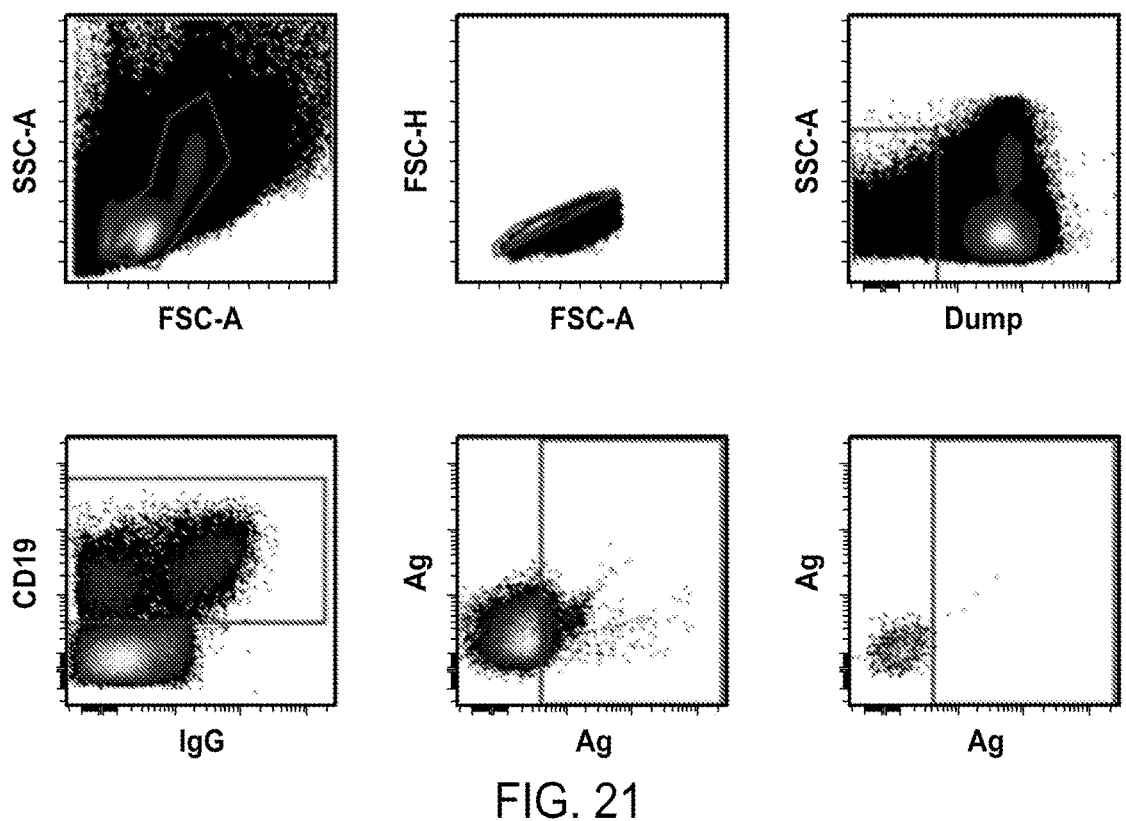
FIG. 21 shows flow sorting strategy to identify virus-specific antibodies from donor 45. To demonstrate the ability of LIBRA-seq to identify ligand-blocking antibody sequences from an HIV infection sample, a panel of 3 oligo-labeled HIV envelope antigens and oligo-labeled soluble CD4 antigen were utilized to stain PBMCs from NIH Donor 45. NIH Donor 45 was chosen for investigation due to the number of previously characterized CD4bs antibody lineages identified in this donor.
Figure 22:
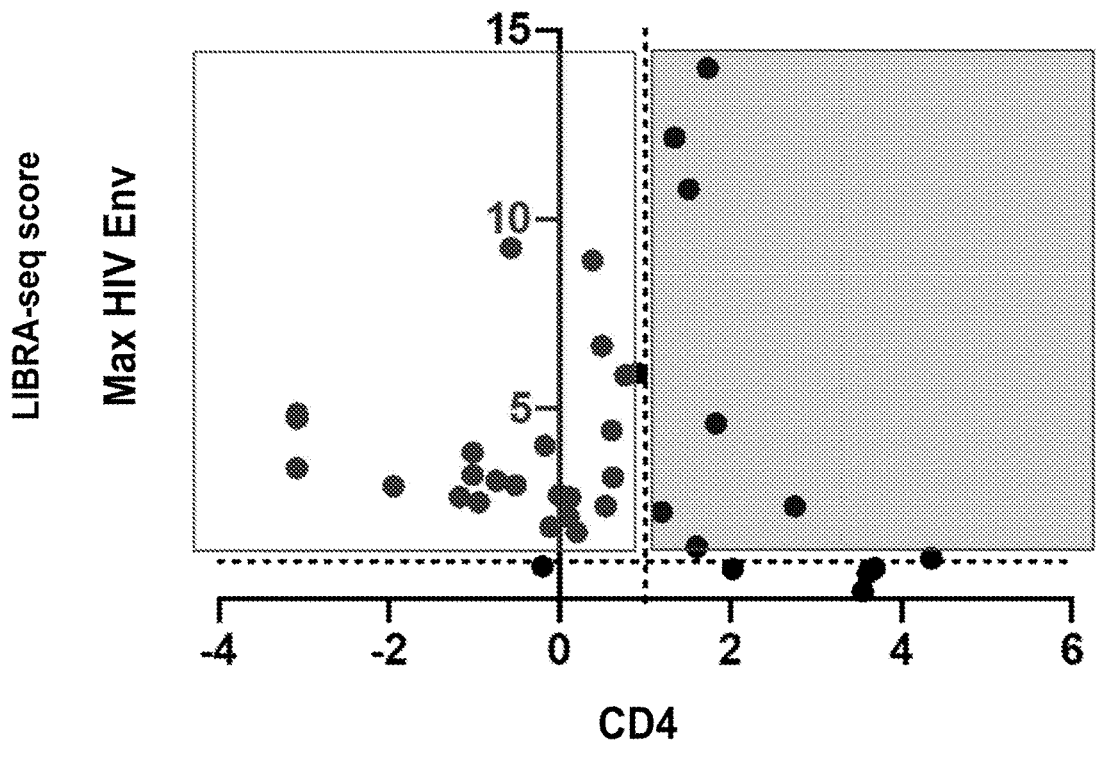
FIG. 22 shows distribution of LIBRA-seq scores identifies cd4bs-specific b cell sequences from donor 45. Plot of maximum LIBRA-seq score (LSS) for a single HIV antigen used in the experiment vs. CD4 LSS where every dot represents a single cell. Cells considered HIV Ag+CD4- (shaded red, defined as having an HIV Ag LSS>1 and a CD4 LSS<1) are predicted be CD4bs-specific. Conversely, Cells considered HIV Ag+CD4+ (shaded purple, defined as having an HIV Ag LSS>1 and a CD4 LSS>1) are predicted to recognize the HIV envelope protein outside the CD4bs.

With each of the two strategies, the fluorescently labeled antigens are associated with a single color (independent of antigen). Before sample processing (for example, 10x) and NGS, the B cell-antigen mixtures are subjected to fluorescence-activated cell sorting (FACS), to select for B cells that are bound to the barcoded antigens. For sorting, cells are counted and viability are assessed using Trypan Blue, washed with DPBS supplemented with 1% Bovine serum albumin (DPBS-BSA) through centrifugation at 300 g for 7 minutes, and resuspended in DPBS-BSA and stained with a variety of cell markers including CD3-APCCy7, IgG-FITC, CD19-BV711, CD14-V500, and LiveDead-V500. The fluorescently labeled antigen-oligo conjugates are added to the stain, so antigen-specific sorting can occur. After staining in the dark for 30 minutes at room temperature, cells are washed 3 times with DPBS-BSA at 300 g for 7 minutes. Then, cells are resuspended in DPBS-BSA and analyzed and/or sorted on the flow cytometer/cell sorter. Antigen-specific B cells are taken as: live, CD14− CD3− CD19+ IgG+, and positive for the PE color, with which all barcoded antigens are labeled (FIGS. 11A, 11B, and 12).

Figure 10:
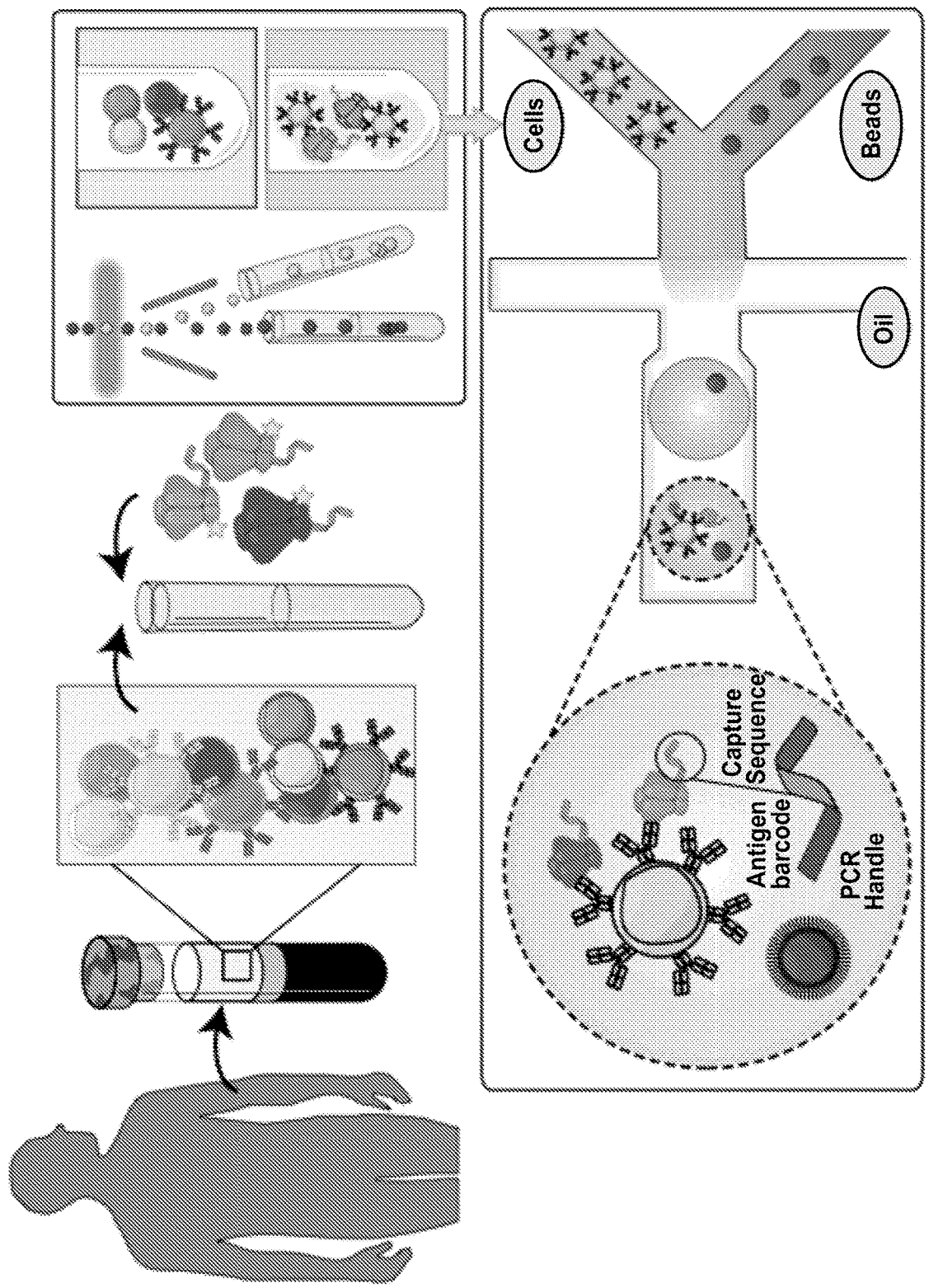
FIG. 10 is a LIBRA-seq assay schematic showing LIBRA-seq with pre-filtering for antigen-bound B cells. Cells of interest are prepared. For example, donor PBMCs are isolated from blood. Then, PBMCs are stained with a panel of DNA-barcoded, fluorescently labeled antigens. DNA-barcoded antigens are labeled with fluorescently labeled streptavidin. (Alternatively, fluorescently labeled oligo barcodes can be used in the antigen-oligo barcoding. In this way, antigens are fluorescently labeled for pre-filtering using fluorescence activated cell sorting (FACS)). Fluorescently labeled antigens are mixed with cells of interest. Antigen positive cells are sorted via FACS prior to single cell sequencing. Single cell suspensions of antigen positive cells are processed and sequenced.

This method enables the determination of antigen-bound B cells for any antigen in the screening library. For increased robustness, each barcoded antigen can be labeled with two different colors, so that only B cells that are double-positive for both colors are retained. The fluorescent labeling of the antigens does not affect the ability to distinguish between different antigen barcodes in the subsequent single-cell analysis and NGS sequencing experiments. In essence, the fluorescent labeling helps select antigen-bound B cells, whereas the subsequent sequencing of the antigen oligo barcodes helps determine which antigens are bound to each of the sorted antigen-bound B cells. The primary difference from non-fluorescent antigen experiments is that only antigen-bound B cells are sequenced here, thus increasing the efficiency and the amount of information that can be obtained from a single sequencing experiment. This filtering step focuses in on rare populations of antigen-specific B cells, ensuring that maximum information is extracted for B cells that have specificity for any of the antigens in the screening library (FIG. 10). If desired, non-antigen-specific B cells from the same sample can also be subjected to separate prep (for example 10x) and sequencing, to maximize the amount of BCR sequence information extracted from a given sample.

Example 5. LIBRA-Seq Methods

Following a LIBRA-seq experiment, there are 2 resulting pairs of FASTQ files: (1) B cell receptor libraries (containing heavy and light chain contigs), and (2) antigen barcode libraries (containing antigen-identifying DNA barcode sequences from the antigen screening library). In some embodiments, it should be understood that the methods described herein are for uniting the information from these two sequencing libraries. Accordingly, in some embodiments, the above noted step of removing a sequence lacking the cell barcode, the UMI, or the antigen barcode is for removing a sequence from the antigen barcode library lacking the cell barcode, the UMI, or the antigen barcode. The methods describe here are for processing the antigen barcodes. The processing serves two purposes: (1) quality control and annotation of sequenced reads, and (2) identification of binding signal from the annotated sequenced reads. Before the following steps are carried out, the BCR libraries are processed in order to determine the list of cell barcodes that have a VDJ sequence.

Processing of antigen barcode reads and BCR sequence contigs. A pipeline shown herein takes paired-end fastq files of oligo libraries as input, processes and annotates reads for cell barcode, UMI, and antigen barcode, and generates a cell barcode-antigen barcode UMI count matrix. BCR contigs can be processed using cellranger (10× Genomics) using GRCh38 as reference. For the antigen barcode libraries, initial quality and length filtering is carried out by fastp (Chen et al., 2018) using default parameters for filtering. This results in only high-quality reads being retained in the antigen barcode library. In a histogram of insert lengths, this results in a sharp peak of the expected insert size of 52-54. Fastx_collapser is then used to group identical sequences and convert the output to deduplicated fasta files. Then, having removed low-quality reads, just the R2 sequences were processed, as the entire insert is present in both R1 and R2. Each unique R2 sequence (or R1, or the consensus of R1 and R2) was processed one by one using the following steps:

(1) The reverse complement of the R2 sequence is determined (Skip step 1 if using R1).
(2) The sequence is screened for possessing an exact (or near exact) match to any of the valid cell barcodes present in the filtered_contig.fasta file output by cell ranger during processing of BCR V(D)J fastq files. Sequences without a BCR-associated cell barcode are discarded.
(3) The 10 bases immediate 3' to the cell barcode are annotated as the read's UMI.
(4) The remainder of the sequence 3' to the UMI is screened for a 13 or 15 bp sequence with a hamming distance of 0, 1, or 2 to any of the antigen barcodes used in the screening library. Following this processing, only sequences around the expected lengths are retained (the lengths of sequences can be from more than 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 bases shorter to more than 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 bases longer than the expected lengths), thus allowing for a deletion, an insertion outside the cell barcode, or bases flanking the cell barcode.

This general process requires that sequences possess all elements needed for analysis (cell barcode, UMI, and antigen barcode), but is permissive to insertions or deletions in the TSO region between the UMI and antigen barcode. After processing each sequence one-by-one, cell barcode-UMI-antigen barcode collisions are screened. Any cell barcode-UMI combination (indicative of a unique oligo molecule) that has multiple antigen barcodes associated with it is removed. A cell barcode-antigen barcode UMI count matrix is then constructed, which served as the basis of subsequent analysis. Additionally, the BCR contigs are aligned (filtered_contigs.fasta file output by Cellranger) to IMGT reference genes using HighV-Quest (Alamyar et al., 2012). The output of HighV-Quest is parsed using ChangeO (Gupta et al., 2015), and merged with the UMI count matrix.

The above stated procedure can be summarized as the following steps:
1) Remove low quality reads;
2) Remove reads too long or too short to be a valid antigen barcode read containing a cell barcode, UMI, and antigen barcode;
3) For each quality read, annotate:
   a. Cell barcode,
   b. UMI
   c. Antigen barcode, allowing for sequencing/PCR errors by using a hamming distance threshold.

Determination of LIBRA-seq Score. Starting with the UMI count matrix, all counts of more than one UMIs (for example, more than 1, 2, 3, 4, 5, 6, 7, 8, 9, 10, 11, 12, 13, 14, 15, 16, 17, 18, 19, 20, etc. UMIs) can be set to 0, with the idea that these low counts can be attributed to noise. After this, the UMI count matrix was subset to contain only cells with a count of one or more UMIs than the minimum value in the above noted step of noise filtering for at least 1 antigen. The centered-log ratios (CLR) of each antigen UMI count for each cell were then calculated (Mimitou et al., 2019; Stoeckius et al., 2017, 2018). Because UMI counts were on different scales for each antigen, due to differential oligo loading during oligo-antigen conjugation, the CLRs UMI counts were rescaled using the StandardScaler method in scikit learn (Pedregosa and Varoquaux, 2011). Lastly, A correction procedure was performed to the z-score-normalized CLRs from UMI counts of 0, setting them to the minimum for each antigen for donor NIAID 45 and N90 experiments, and to −1 for the Ramos B cell line experiment. These CLR-transformed, Z-score-normalized, corrected values served as the final LIBRA-seq scores. LIBRA-seq scores were visualized using Cytobank (Kotecha et al., 2010).

Identification of sequence feature—antigen specificity associations. Following determination of LIBRA-seq scores (above), and because antibody sequence is united with antigen specificity (in the form of a LIBRA-seq score), sequence-specificity associations can be made.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A method for simultaneous detection of an antigen and an antibody that specifically blocks an interaction between said antigen and a ligand thereof, comprising:
   labeling a plurality of antigens with unique antigen barcodes;
   providing a plurality of barcode-labeled antigens to a population of B-cells to form a mixture;
   allowing the plurality of barcode-labeled antigens to bind to the population of B-cells;
   labeling one or more ligands to one or more antigens in the plurality of antigens with unique ligand barcodes;
   introducing the one or more ligands to the mixture of the plurality of barcode-labeled antigens and the population of B-cells;
   washing unbound antigens from the population of B-cells;
   separating the B-cells into single cell emulsions;
   introducing into each single cell emulsion a unique cell barcode-labeled bead;
   preparing a single cell cDNA library from the single cell emulsions;
   performing PCR amplification reactions to produce a plurality of amplicons, wherein the amplicons comprise: 1) the cell barcode and the antigen barcode, 2) the cell barcode and an antibody sequence, and 3) the cell barcode and the ligand barcode, and wherein each amplicon comprises a unique molecular identifier (UMI);
   sequencing the plurality of amplicons;
   removing a sequence lacking the cell barcode, the UMI, the ligand barcode, or the antigen barcode;
   aligning the antibody sequence to a reference library of immunoglobulin V, D, J and C sequences;
   constructing a first UMI count matrix comprising the cell barcode, the antigen barcode, and the antibody sequence and a second UMI count matrix comprising the cell barcode, the ligand barcode, and the antibody sequence;
   determining a first LIBRA-seq score according to the first UMI count matrix and a second LIBRA-seq score according to second UMI count matrix; and
   determining that the antibody blocks the interaction between the antigen and the ligand if the first LIBRA-seq score is higher in comparison to a first reference level and the second LIBRA-seq score is lower in comparison to a second reference level.

2. The method of claim 1, wherein the barcode-labeled antigens are labeled with a first barcode comprising a DNA sequence or an RNA sequence.

3. The method of claim 1, wherein the cell barcode-labeled beads are labeled with a second barcode comprising a DNA sequence or an RNA sequence.

4. The method of claim 1, wherein the antibody sequence comprises an immunoglobulin heavy chain (VDJ) sequence, or an immunoglobulin light chain (VJ) sequence.

5. The method of claim 1, wherein the barcode-labeled antigens comprise a membrane-anchored antigen.

6. The method of claim 1, wherein the barcode-labeled antigens comprise an antigen from a pathogen or an animal.

7. The method of claim 6, wherein the antigen is not purified.

8. The method of claim 6, wherein the antigen from a pathogen comprises an antigen from a virus.

9. The method of claim 8, wherein the antigen from a virus comprises an antigen from human immunodeficiency virus (HIV), an antigen from influenza virus, or an antigen from respiratory syncytial virus (RSV).

10. The method of claim 1, further comprising determining a level of somatic hypermutation of the antibody specifically binding to the antigen.

11. The method of claim 1, further comprising determining a length of a complementarity-determining region (CDR) of the antibody specifically binding to the antigen.

12. The method of claim 1, further comprising determining a motif of a CDR of the antibody specifically binding to the antigen.

13. The method of claim 11, wherein the CDR is selected from the group consisting of CDRH1, CDRH2, CDRH3, CDRL1, CDRL2, and CDRL3.

14. A method for simultaneously screening an antigen and an antibody that specifically binds said antigen, comprising:
   generating a plurality of antigens using an antigen display technology, wherein each of the plurality of antigens is linked to a nucleic acid sequence that identifies a particular antigen;
   providing the plurality of antigens to a population of B-cells;
   allowing the plurality of antigens to bind to the population of B-cells;
   washing unbound antigens from the population of B-cells;
   separating the B-cells into single cell emulsions;
   introducing into each single cell emulsion a unique cell barcode-labeled bead;
   preparing a single cell cDNA library from the single cell emulsions;
   performing PCR amplification reactions to produce a plurality of amplicons, wherein the amplicons comprise: 1) the cell barcode and the nucleic acid sequence that identifies the particular antigen, and 2) the cell barcode and an antibody sequence, and wherein each amplicon comprises a unique molecular identifier (UMI);
   sequencing the plurality of amplicons;
   removing a sequence lacking the cell barcode, the UMI, or the nucleic acid sequence that identifies the particular antigen;
   aligning the antibody sequence to a reference library of immunoglobulin V, D, J and C sequences;
   constructing a UMI count matrix comprising the cell barcode, the nucleic acid sequence that identifies the particular antigen, and the antibody sequence;
   determining a LIBRA-seq score;
   determining the nucleic acid sequence that identifies the particular antigen; and determining that the antibody specifically binds an antigen if the LIBRA-seq score of the antibody for the antigen is higher than a reference level.

15. The method of claim 14, wherein the plurality of antigens are labeled with a first barcode comprising a DNA sequence or an RNA sequence.

16. The method of claim 14, wherein the cell barcode-labeled beads are labeled with a second barcode comprising a DNA sequence or an RNA sequence.

17. A method for determining a binding potency of an antibody to an antigen, comprising:
- labeling a plurality of antigens with unique antigen barcodes;
- providing a plurality of barcode-labeled antigens to a population of B-cells;
- allowing the plurality of barcode-labeled antigens to bind to the population of B-cells;
- washing unbound antigens from the population of B-cells;
- separating the B-cells into single cell emulsions;
- introducing into each single cell emulsion a unique cell barcode-labeled bead;
- preparing a single cell cDNA library from the single cell emulsions;
- performing PCR amplification reactions to produce a plurality of amplicons, wherein the amplicons comprise: 1) the cell barcode and the antigen barcode, and 2) the cell barcode and an antibody sequence, and wherein each amplicon comprises a unique molecular identifier (UMI);
- sequencing the plurality of amplicons;
- removing a sequence lacking the cell barcode, the UMI, or the antigen barcode;
- aligning the antibody sequence to a reference library of immunoglobulin V, D, J and C sequences;
- constructing a UMI count matrix comprising the cell barcode, the antigen barcode, and the antibody sequence;
- determining a LIBRA-seq score; and
- determining that the antibody has a high binding potency to the antigen if the LIBRA-seq score of the antibody for the antigen is higher than a reference level.

* * * * *